US006770741B1

(12) United States Patent
Kyle et al.

(10) Patent No.: US 6,770,741 B1
(45) Date of Patent: Aug. 3, 2004

(54) BRANDYKININ ANTAGONIST PEPTIDES

(75) Inventors: Donald James Kyle, Abingdon, MD (US); Roger Neal Hiner, Baltimore, MD (US)

(73) Assignee: Scios Inc., Sunnyvale, CA (US)

(*) Notice: Subject to any disclaimer, the term of this patent is extended or adjusted under 35 U.S.C. 154(b) by 0 days.

(21) Appl. No.: 08/359,642

(22) Filed: Dec. 20, 1994

Related U.S. Application Data

(63) Continuation of application No. 08/167,052, filed on Dec. 16, 1993, now Pat. No. 5,385,889, which is a continuation of application No. 07/866,246, filed on Apr. 14, 1992, now abandoned, which is a continuation-in-part of application No. 07/687,959, filed on Apr. 19, 1991, now abandoned.

(51) Int. Cl.$^7$ ..................... A61K 38/00; A61K 38/11; C07K 16/00
(52) U.S. Cl. ..................... 530/314; 530/328; 530/332; 514/15; 514/803
(58) Field of Search ..................... 530/314, 328; 514/15, 20, 2, 803; 930/30; 435/107; 548/532

(56) References Cited

U.S. PATENT DOCUMENTS

| 4,242,329 A | 12/1980 | Claeson et al. | 424/177 |
| 4,483,850 A | 11/1984 | Patchett et al. | 424/177 |
| 4,693,993 A | 9/1987 | Stewart et al. | 514/14 |
| 4,801,613 A | 1/1989 | Stewart et al. | 514/14 |
| 4,822,894 A | 4/1989 | Geiger et al. | 548/252 |
| 4,923,963 A | 5/1990 | Stewart et al. | 530/314 |

FOREIGN PATENT DOCUMENTS

| WO | 370453 | 5/1990 |
| WO | 413277 | 2/1991 |

OTHER PUBLICATIONS

Karanewsky et al., "(Phosphinyloxy) acyl Amino Acid Inhibitors of Angiotensin Converting Enzyme. 2. Terminal Amino Acid Analogues of (S)–1–[6–Amino–2–[hydroxy (4–phenylbutyl) phosphinyl]oxy]–1–oxohexyl–L–proline," *Journal of Medicinal Chemistry*, vol. 33, No. 5 (1990), pp. 1459–1469.

Smith et al., "Synthesis and Pharmacological Activity of Angiotensin Converting Enzyme Inhibitors: N–(Mercapto–acyl)–4–substituted–(S) –prolines," *Journal of Medicinal Chemistry*, vol. 31, No. 4 (1988), pp. 875–885.

Krapcho et al., "Angiotensin–Converting Enzyme Inhibitors. Mercaptan, Carboxyalkyl Dipeptide, and Phosphinic Acid Inhibitors Incorporating 4–Substituted Prolines," *Journal of Medicinal Chemistry*, vol. 31, No. 6 (1988), pp. 1148–1160.

Hock et al., "Hoe 140 A New Potent and Long Acting Bradykinin–Antagonist: in vitro studies", *Br. J. Pharmacol.*, vol. 102, pp. 769–774 (1991).

Wirth et al., "Hoe 140 A New Potent and Long Acting Bradykinin–Antagonist: in vivo studies", *Br. J. Pharmacol.*, vol. 102, pp. 774–777 (1991).

Pongracic et al., "A Competitive Kinin Receptor Antagonist, [DArg$^0$, Hyp$^3$, DPhe$^7$]–Bradykinin, Does Not Affect the Response to Nasal Provocation with Bradykinin", *Br. J. Pharmacol.*, vol. 31, pp. 287–294 (1991).

Higgins et al., "A Study of the Efficacy of the Bradykinin Antagonist NPC567 in Rhinovirus infections in Human Volunteers", *Chemical Abstracts* #114: 220805d (1991).

Soler et al., "A Bradykinin Antagonist Modifies Antigen–Induced Airway Hyper–Responsiveness and Airway Inflammation in Allergic Sheep", *Am. Rev. Respir. Dis.* A327 (1989).

John M. Stewart, "Hydroxyproline Analogs of Bradykinin" *Journal of Medicinal Chemistry* (1974) vol. 17, No. 5 pp. 537–539.

J.M. Stewart, "Chemistry and Biologic Activity of Peptides Related to Bradykinin" *Handbook of Experimental Pharamcol. vol. XXV Supp, Springer–Verlag Berlin* Heidelberg NY (1979).

J. Barabe et al. "New Agonist and Antagonist Analogues of Bradykinin", *Can. J. Physiol. Pharmacol.*, vol. 62, 1984 pp. 627–629.

Raymond J. Vavrek, et al., "Smooth Muscle Selectivity in Bradykinin Analogs with Multiple D–Amino Acid Substitutions", Dept. of Biochem., Univ. of Colorado School of Medicine, Denver, Colorado 1986.

J. Rifo et al., "Bradykinin Receptor Antagonists Used To Characterize the Heterogeneity of Bradykinin–induced Responses in Rat vas Deferens" *European Journal of Pharmacology*, 142 (1987), pp. 305–312.

I.J. Zeitlin et al., "Mobilization of Tissue Kallikrein in Inflammatory Disease of the Colon," Wolfson Labs; Gastrointestinal Unit, West. Gen. Hosp. and Dept. of Clinical Surgery, Univ. of Edinburgh (1972), pp. 133–138.

Kenji Suzuki et al., "Synthesis of Every Kinds of Peptide Fragments of Bradykinin" *Chemical Pharm. Bull.* (1969) vol. 17, pp. 1671–1678.

*Primary Examiner*—Jyothsna Venkat
*Assistant Examiner*—Tomas Friend
(74) *Attorney, Agent, or Firm*—Nath & Associates PLLC; Gary M. Nath; Todd L. Juneau

(57) ABSTRACT

The substitution of the L-Pro at the 7-position of the peptide hormone bradykinin or other substituted analogs of bradykinin with a D-configuration hydroxyproline ether or thioether converts bradykinin agonists into bradykinin antagonists. The invention further includes the intermediate compounds and additional modifications at other positions within the novel 7-position modified bradykinin antagonists which increase enzyme resistance, antagonist potency, and/ or specificity of the new bradykinin antagonists. The analogs produced are useful in treating conditions and diseases of a mammal and human in which an excess of bradykinin or related kinins are produced or injected such as by insect bites.

4 Claims, 3 Drawing Sheets

TABLE 1

Figure 1:
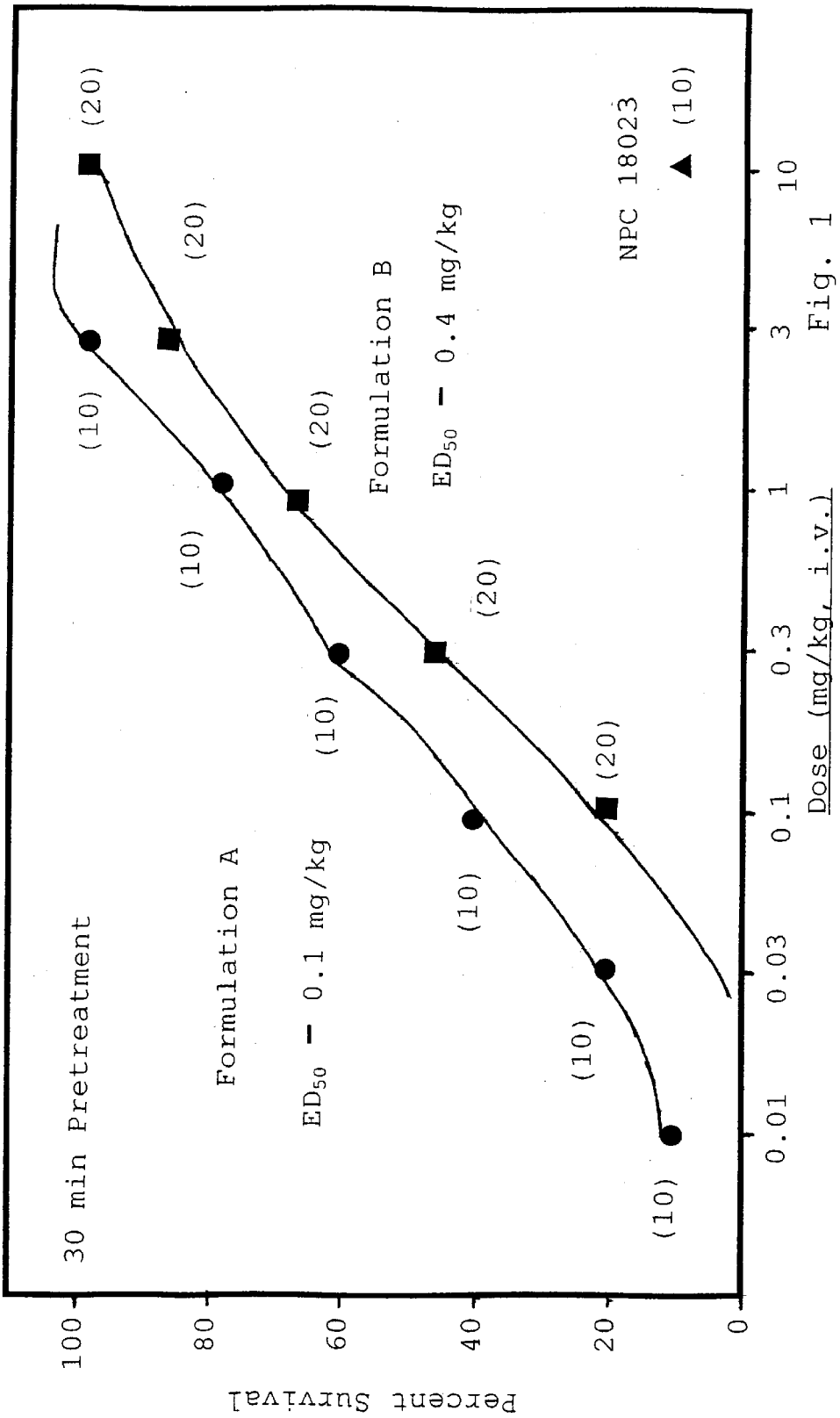

IN VIVO PHARMACOLOGY
GRAM NEGATIVE SEPSIS (THERAPEUTIC-ADMINISTRATION IN RATS)

| Treatment Group | Time (hr) of Drug Administration After Sepsis Induction | Survival (n) |
|---|---|---|
| Gentamicin + Vehicle | – | 28 hr ± 1 (9) |
| Gentamicin + Formulation A (1 mg/kg/hr for 4 hr) | 0.5 | > 2 wk (2) |
| | 1 | 49 hr (1)<br>> 2 wk (8) |
| | 6 | > 2 wk (8) |
| | 12 | 25 hr (1)<br>31 - 46 hr (1)<br>> 2 wk (4) |
| | 18 | 28 ± 1 hr (4) |

TABLE 2

IN VIVO PHARMACOLOGY
GRAM NEGATIVE SEPSIS (CO-ADMINISTRATION IN RATS)

| Treatment Group | Infusion Time (hr) | Total Dose Administered (mg/kg) | Survival (n) |
| --- | --- | --- | --- |
| Gentamicin + Vehicle | | – | 28 hr ± 1 (9) |
| Gentamicin + Formulation A (1 mg/kg) | 4 | 5 | 48-72 hr (1) > 2 wk (5) |
| | 2 | 3 | 54-69 hr (1) > 2 wk (4) |
| Gentamicin + Formulation A (0.3 mg/kg) | 4 | 1.5 | 44 hr (1) > 2 wk (3) |
| Gentamicin + Formulation A (0.1 mg/kg) | 4 | 0.5 | 36 ± 4 hr (4) |

BRANDYKININ ANTAGONIST PEPTIDES

This application is a continuation of U.S. patent application Ser. No. 08/167,052 filed Dec. 16, 1993, now U.S. Pat. No. 5,385,889, the entire contents of which are hereby incorporated by reference, which is a continuation of U.S. patent application Ser. No. 07/866,246 filed Apr. 14, 1992, now abandoned, which is a continuation-in-part of U.S. patent application Ser. No. 07/687,959 filed Apr. 19, 1991, now abandoned.

BACKGROUND OF THE INVENTION

1. Field of the Invention

This invention relates to compounds which are bradykinin receptor antagonists, pharmaceutical compositions and methods for using these compounds to antagonize the effects of bradykinin in mammals, including humans. More particularly, the invention relates to the substitution of the L-Pro at position 7 with D-hydroxyproline ether or thioether compounds and its intermediate product which convert bradykinin agonists into antagonists and also includes additional modifications at other positions within the 7-position modified bradykinin antagonist which confer increased antagonist potency, resistance to enzymatic degradation, and/or tissue specificity on the D-amino acid-containing bradykinin sequence.

2. Description of the Prior Art

Bradykinin (BK) is a nonapeptide generated as a result of the activity of kallikreins, a group of proteolytic enzymes present in most tissues and body fluids, on kininogens. Once released, kinins produce many physiological responses, including pain and hyperanalgesia by stimulating C- and A-fibers in the periphery. There is also considerable evidence that kinins contribute to the inflammatory response.

Bradykinin, and its physiologically important related peptides kallidin (Lys-bradykinin) and Met-Lys-bradykinin, exhibit physiological actions which qualify them as mediators of inflammatory reactions, hypotensive states, and pain. Bradykinin is overproduced in pathological conditions such as septic shock, anaphylaxis, rhinitis, asthma, inflammatory bowel disease, and certain other conditions including acute pancreatitis, post-gastrectomy dumping syndrome, carcinoid syndrome, migraine, and angioneurotic edema. The production of bradykinin from the plasma results in pain at the site of the pathological condition, and the overproduction intensifies the pain directly or via bradykinin-induced activation of the arachidonic acid pathway which produces prostaglandins and leukotrienes, the more distal and actual mediators of inflammation.

In addition to its analgesic and proinflammatory effects, bradykinin is a vasodilator. Because of its ability to lower blood pressure, bradykinin has been implicated in the pathogenesis of several shock syndromes, particularly septic or endotoxic shock. Bradykinin is also a potent bronchoconstrictor in animals and asthmatic subjects and it has been implicated as a contributor to the pathogenesis of airway inflammatory conditions such as allergic asthma and rhinitis.

Thus, a bradykinin inhibitor or bradykinin receptor antagonist is expected to possess a number of desirable biological effects in the treatment, for example, of inflammation, septic shock, asthma, burn pain, rhinitis, and allergy.

The search for understanding the mechanism of action of bradykinin, which is essential for the development of useful tools for diagnostic use, and for the development of therapeutic agents aimed at alleviating the intense pain caused by the production and overproduction of bradykinin, has been hindered by the lack of specific sequence-related competitive antagonists of bradykinin.

Several non-peptide, non-specific and non-selective antagonists of one or more of the biological activities of bradykinin have been described among compounds as diverse as analgesics and anti-inflammatory substances, which act via the prostaglandin system and not directly on bradykinin receptors. These are antihistamines; bradykinin-antibodies; benzodiazepine derivatives; high molecular weight ethylene oxide polymers; gallic acid esters; and serotonin inhibitors. None of these compounds or classes of compounds specifically inhibit the effects of bradykinin.

Heptyl esters of various amino acid-containing substances, such as single basic amino acids, the dipeptide Phe-Gly, and analogs of C-terminal peptide fragments of bradykinin (i.e., Pro-Phe-Arg) have been reported as anti-bradykinin substances. When tested in bradykinin assay systems, they prove to be weak partial agonists/antagonists, depending on the dose, with little specificity for inhibiting bradykinin action.

Preparations of damaged vascular tissue have been reported to respond to bradykinin analogs which lack the C-terminal arginine residue, but not to bradykinin itself, and analogs of these des-Arg(9)-bradykinins have been developed as antagonists for the non-physiological activity of bradykinin. These antagonists have no significant bradykinin-like agonist effects, nor any antagonist effect on any of the physiologically significant kinin-responding systems. Furthermore, several bradykinin analogs containing the O-methyl ether of Tyr residues at positions 5 and/or 8 have been reported to produce mixed agonist/antagonist activity on isolated uteri of galactosemic rats, but not on normal rats.

Other changes in the bradykinin molecule have been additions of amino acids at the N-terminal end which affect the rate of enzymatic degradation of bradykinin in vivo.

It has been reported that the half life of bradykinin in the systemic circulation is less than 30 seconds. Bradykinin appears to be completely destroyed (98–99% destruction) on a single passage through the pulmonary circulation as determined in an anesthetized rat by measuring the depressor effects of an agonist following intra-aortic (IA) (bypassing the pulmonary circulation) and intravenous (IV) administration. Resistance of bradykinin agonists to pulmonary kininase destruction in vivo also appears promoted by addition of single (i.e., D-Arg-, D-Lys-, Lys-) and double (D-Lys-Lys-) basic amino acid residues to the N-terminal of the bradykinin sequence. The addition of the dipeptide Lys—Lys to the N-terminal of bradykinin agonists has been reported to confer complete resistance to in vivo destruction on initial passage through the pulmonary circulation.

Several research groups have prepared bradykinin receptor antagonists. Stewart and Vavrek in U.S. Pat. No. 4,801, 613, (which reference is incorporated in its entirety herein) disclose a series of bradykinin antagonists wherein the L-Pro at the 7-position of the peptide hormone bradykinin or other substituted analogs of bradykinin is substituted with an aromatic amino acid of the D-configuration which converts bradykinin agonists into bradykinin antagonists. The analogs produced are useful in treating conditions and diseases of a mammal and human in which an excess of bradykinin or related kinins are produced or injected as by insect bites into the body. The specific L-Pro substitutions are selected from the group consisting of D-Nal, D-PNF, D-Phe, D-Tyr, D-Pal, D-OMT, D-Thi, D-Ala, D-Trp, D-His, D-Homo-Phe, D-Phe, pCl-D-Phe (CDF), D-Phg, D-Val, D-Ile, D-Leu, and MDY.

In U.S. Pat. No. 4,693,993, also to Stewart and Vavrek, additional L-Pro substitution materials are disclosed.

Copending application Ser. No. 08/167,051, filed Dec. 16, 1993, which is a continuation of application Ser. No. 07/866,385 filed Apr. 14, 1992, which in turn was a continuation-in-part of Ser. No. 07/687,950 filed Apr. 19, 1991, discloses and claims additional L-Pro substitution materials with hydroxyproline ether and thioether compounds.

U.S. Pat. No. 4,242,329 to Claeson et al. disclose the formation of Bradykinin-inhibiting tripeptide derivatives. A process for producing said tripeptide derivatives by synthesis and purification methods which are known in the peptide chemistry is also disclosed as well as pharmaceutical preparations comprising the tripeptide derivative.

Published European Patent Applications No. 0 413 277 A1 and 0 370 453 AZ disclose bradykinin antagonists.

SUMMARY OF THE INVENTION

The present invention resides in the discovery that the novel compounds identified below, are potent bradykinin receptor antagonists. The compounds are useful in the treatment of various diseases including inflammatory disorders, asthma, septic shock, and burn pain. Included in the invention are pharmaceutical compositions containing the inventive compounds and methods of using the compounds as bradykinin receptor antagonists.

More particularly, the invention relates to the modification of the sequence of the mammalian peptide hormone bradykinin (Arg Pro Pro Gly Phe Ser Pro Phe Arg), SEQ ID NO 1, and pharmaceutically acceptable salts thereof, at the Pro residue at position 7 in a unique manner which produces sequence-related analogues that act as specific and competitive inhibitors of the biological activities of bradykinin. The invention specifically relates to the substitution of the L-Pro at position 7 with a material having the D-configuration (*) and the formula:

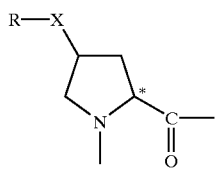

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either $SO_n$ or oxygen, and n=0, 1, or 2; and pharmaceutically acceptable salts thereof.

More specifically, the invention relates to the formation of peptides having the formula:

N-A-B-C-D-E-F-G-H-I-J-Cn wherein N is hydrogen;
A and B are independently selected from the group consisting of L-Arg, D-Arg, D-Gln, L-Gln, D-Asn, L-Asn, N-ε-acetyl-D-lysine, ε-acetyl-L-lysine, NG-p-tosyl-Arg, NG-nitro-Arg, Lys—Lys, acetyl-D-Arg, L-Citrulline, L-Lys, Sar, and D-Lys;

C and D are a direct bond or are independently selected from the group consisting of Pro, dehydroPro, 4Hyp, Tic, Aoc, L-azetidine-2-carboxylic acid, Eac, Gly, Thz, Oic, Ala, and Aib;

E is a direct bond or is selected from the group consisting of Gly, Ala, Thr, and Ser;

F is selected from the group consisting of Phe, Thi, Leu, Ile, Tic, Oic, homoPhe, phenylGly, β-cyclohexylalanine, Nal, and Val;

G is a direct bond or is selected from the group consisting of Ser, Thr, 4Hyp, Gly, Val, and Ala;

H is a compound of the D-configuration having the formula:

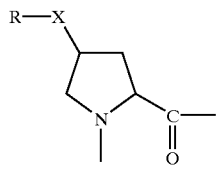

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either $SO_n$ or oxygen, and n=0, 1, or 2;

I is selected from the group consisting of Oic, Aoc, Thz, Tic, L-indoline-2-carboxylic acid, octahydro-1H-isoindole-1-carboxylic acid, pipecolinic acid, Pro, 4Hyp, azetidine-2-carboxylic acid, Aib, Leu, Ile, Val, Thi, Phe, homoPhe, and compounds of the following formula:

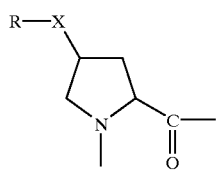

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $RNHC(o)$— where $R^1$ is $C_1$–$C_6$ alkyl or aryl, and where X is either $SO_n$ or oxygen, and n=0, 1, or 2;

J is selected from the group consisting of Arg, Orn, Asn, Gln, N-ε-acetyl-Lys, N-δ-acetyl-Orn, and Lys;

Cn is a hydroxyl group or a C-terminal extension is selected from the group consisting of amide, alkoxy group, an acidic, basic or neutral aliphatic, aromatic, cyclic amino acid residue of the D- or L-configuration, and a peptide extension composed of D- or L-amino acids; and pharmaceutically acceptable salts thereof.

A particularly preferred material is a peptide wherein:
N is hydrogen;
A and B are independently selected from the group consisting of L-Arg, D-Arg, Lys—Lys, Lys;
C and D are independently selected from the group consisting of Pro, dehydroPro, and 4Hyp;
E is Gly;

F is selected from the group consisting of Phe, Thi, Leu, and β-cyclohexylalanine;

G is a direct bond or is selected from the group consisting of Ser and Thr;

H is a compound of the D-configuration having the formula:

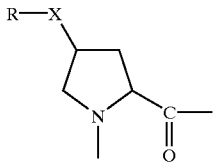

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either $SO_n$ or oxygen, and n=0, 1, or 2;

I is selected from the group consisting of Oic, Aoc, Thz, Pro, pipecolinic acid, Leu, Phe, Thi, Tic, and compounds of the formula:

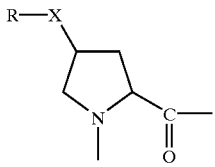

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group and a group of the formula $R^1NHC(o)$— where $R^1$ is $C_1$–$C_6$ alkyl or aryl, and where X is either $SO_n$ or oxygen, and n=0, 1, or 2;

J is selected from the group consisting of Arg and Lys;

Cn is a hydroxyl group;

and pharmaceutically acceptable salts thereof.

Another preferred material is a peptide wherein:

N is hydrogen;

A is D-Arg;

B is Arg;

C is Pro;

D is selected from the group consisting of Pro and 4Hyp;

E is Gly;

F is selected from the group consisting of Phe, Leu, and Thi;

G is a direct bond or is Ser;

H is a compound of the D-configuration having the formula:

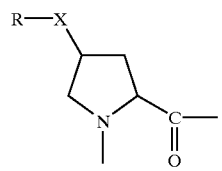

wherein R is selected from the group consisting of methyl, ethyl, propyl, isobutyl, cyclohexylmethyl, allyl, methallyl, prenyl, benzyl, phenyl, nitrophenyl, napthal, chlorophenyl, 4-methylphenyl, 3-phenylpropyl, phenylpropyl, and methylbutyl, and where X is $SO_n$ or oxygen, and n=0, 1, or 2;

I is selected from the group consisting of Oic, Aoc, Thz, Tic, and compounds of the formula:

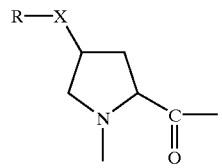

wherein R is selected from the group consisting of methyl, ethyl, propyl, isobutyl, cyclohexylmethyl, allyl, methallyl, prenyl, benzyl, phenyl, 4-chlorophenyl, 4-methylphenyl, and phenylcarbamoyl and where X is either $SO_n$ or oxygen, and n=0, 1, or 2;

J is Arg;

Cn is a hydroxyl group;

and pharmaceutically acceptable salts thereof.

The present invention also includes the intermediate compound having the D-trans formula:

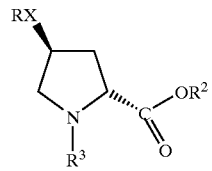

Preferred peptides according to the invention include the following nonlimiting materials:

Hyp Pro Alkyl Ethers and Substituted Alkyl Ethers

D-Arg-Arg-Pro-4Hyp-Gly-Thi-Ser-(D-4-Hydroxyproline trans methyl ether)-Tic-Arg

D-Arg-Arg-Pro-4Hyp-Gly-Thi-Ser-(D-4-hydroxyproline cis methyl ether)-Tic-Arg

D-Arg-Arg-Pro-4Hyp-Gly-Thi-Ser-(D-4-Hydroxyproline trans ethyl ether)-Tic-Arg

D-Arg-Arg-Pro-4Hyp-Gly-Thi-Ser-(D-4-Hydroxyproline trans propyl ether)-Tic-Arg

D-Arg-Arg-Pro-4Hyp-Gly-Thi-Ser-(D-4-hydroxyproline cis propyl ether)-Tic-Arg

D-Arg-Arg-Pro-4Hyp-Gly-Thi-Ser-(D-4-Hydroxyproline trans methyl ether)-Oic-Arg

D-Arg-Arg-Pro-4Hyp-Gly-Thi-Ser-(D-4-Hydroxyproline trans ethyl ether)-Oic-Arg

D-Arg-Arg-Pro-4Hyp-Gly-Phe-Ser-(D-4-hydroxyproline cis ethyl ether)-Oic Arg

D-Arg-Arg-Pro-4Hyp-Gly-Thi-Ser-(D-4-Hydroxyproline trans propyl ether)-Oic-Arg

D-Arg-Arg-Pro-4Hyp-Gly-Thi-Ser-(D-4-Hydroxyproline trans methyl ether)-Aoc-Arg

D-Arg-Arg-Pro-4Hyp-Gly-Thi-Ser-(D-4-Hydroxyproline trans ethyl ether)-Aoc-Arg
D-Arg-Arg-Pro-4Hyp-Gly-Thi-Ser-(D-4-Hydroxyproline trans propyl ether)-Aoc-Arg
D-Arg-Arg-Pro-4Hyp-Gly-Phe-Ser-(D-4-Hydroxyproline trans methyl ether)-Tic-Arg
D-Arg-Arg-Pro-4Hyp-Gly-Phe-Ser-(D-4-Hydroxyproline trans ethyl ether)-Tic-Arg
D-Arg-Arg-Pro-4Hyp-Gly-Phe-Ser-(D-4-Hydroxyproline trans propyl ether)-Tic-Arg
D-Arg-Arg-Pro-4Hyp-Gly-Phe-Ser-(D-4-Hydroxyproline trans methyl ether)-Oic-Arg
D-Arg-Arg-Pro-4Hyp-Gly-Phe-Ser-(D-4-Hydroxyproline trans ethyl ether)-Oic-Arg
D-Arg-Arg-Pro-4Hyp-Gly-Phe-Ser-(D-4-Hydroxyproline trans propyl ether)-Oic-Arg
D-Arg-Arg-Pro-4Hyp-Gly-Phe-Ser-(D-4-Hydroxyproline trans methyl ether)-Aoc-Arg
D-Arg-Arg-Pro-4Hyp-Gly-Phe-Ser-(D-4-Hydroxyproline trans ethyl ether)-Aoc-Arg
D-Arg-Arg-Pro-4Hyp-Gly-Phe-Ser-(D-4-Hydroxyproline trans propyl ether)-Aoc-Arg Pro—Pro Alkyl Ethers Arg-Arg-Pro-Pro-Gly-Thi-Ser-(D-4-Hydroxyproline trans methyl ether)-Tic-Arg
D-Arg-Arg-Pro-Pro-Gly-Thi-Ser-(D-4-Hydroxyproline trans ethyl ether)-Tic-Arg
D-Arg-Arg-Pro-Pro-Gly-Thi-Ser-(D-4-Hydroxyproline trans propyl ether)-Tic-Arg
D-Arg-Arg-Pro-Pro-Gly-Thi-Ser-(D-4-Hydroxyproline trans methyl ether)-Oic-Arg
D-Arg-Arg-Pro-Pro-Gly-Thi-Ser-(D-4-Hydroxyproline trans ethyl ether)-Oic-Arg
D-Arg-Arg-Pro-Pro-Gly-Thi-Ser-(D-4-Hydroxyproline trans propyl ether)-Oic-Arg
D-Arg-Arg-Pro-Pro-Gly-Thi-Ser-(D-4-Hydroxyproline trans methyl ether)-Aoc-Arg
D-Arg-Arg-Pro-Pro-Gly-Thi-Ser-(D-4-Hydroxyproline trans ethyl ether)-Aoc-Arg
D-Arg-Arg-Pro-Pro-Gly-Thi-Ser-(D-4-Hydroxyproline trans propyl ether)-Aoc-Arg
D-Arg-Arg-Pro-Pro-Gly-Phe-Ser-(D-4-Hydroxyproline trans methyl ether)-Tic-Arg
D-Arg-Arg-Pro-Pro-Gly-Phe-Ser-(D-4-Hydroxyproline trans ethyl ether)-Tic-Arg
D-Arg-Arg-Pro-Pro-Gly-Phe-Ser-(D-4-Hydroxyproline trans propyl ether)-Tic-Arg
D-Arg-Arg-Pro-Pro-Gly-Phe-Ser-(D-4-Hydroxyproline trans methyl ether)-Oic-Arg
D-Arg-Arg-Pro-Pro-Gly-Phe-Ser-(D-4-Hydroxyproline trans ethyl ether)-Oic-Arg
D-Arg-Arg-Pro-Pro-Gly-Phe-Ser-(D-4-Hydroxyproline trans propyl ether)-Oic-Arg
D-Arg-Arg-Pro-Pro-Gly-Phe-Ser-(D-4-Hydroxyproline trans methyl ether)-Aoc-Arg
D-Arg-Arg-Pro-Pro-Gly-Phe-Ser-(D-4-Hydroxyproline trans ethyl ether)-Aoc-Arg
D-Arg-Arg-Pro-Pro-Gly-Phe-Ser-(D-4-Hydroxyproline trans propyl ether)-Aoc-Arg Arylalkyl Ethers D-Arg-Arg-Pro-4Hyp-Gly-Phe-Ser-(D-4-hydroxyproline trans 3'-phenylpropyl ether)-Oic-Arg Thioalkyl Ethers D-Arg-Arg-Pro-4Hyp-Gly-Thi-Ser-(D-4-trans thiomethylproline)-Tic-Arg
D-Arg-Arg-Pro-4Hyp-Gly-Thi-Ser-(D-4-trans thioethylproline)-Tic-Arg
D-Arg-Arg-Pro-4Hyp-Gly-Thi-Ser-(D-4-trans thiopropylproline)-Tic-Arg
D-Arg-Arg-Pro-4Hyp-Gly-Thi-Ser-(D-4-trans thiomethylproline)-Oic-Arg
D-Arg-Arg-Pro-4Hyp-Gly-Thi-Ser-(D-4-trans thioethylproline)-Oic-Arg
D-Arg-Arg-Pro-4Hyp-Gly-Thi-Ser-(D-4-trans thiopropylproline)-Oic-Arg
D-Arg-Arg-Pro-4Hyp-Gly-Thi-Ser-(D-4-trans thiomethylproline)-Aoc-Arg
D-Arg-Arg-Pro-4Hyp-Gly-Thi-Ser-(D-4-trans thioethylproline)-Aoc-Arg
D-Arg-Arg-Pro-4Hyp-Gly-Thi-Ser-(D-4-trans thiopropylproline)-Aoc-Arg
D-Arg-Arg-Pro-4Hyp-Gly-Phe-Ser-(D-4-trans thiomethylproline)-Tic-Arg
D-Arg-Arg-Pro-4Hyp-Gly-Phe-Ser-(D-4-trans thioethylproline)-Tic-Arg
D-Arg-Arg-Pro-4Hyp-Gly-Phe-Ser-(D-4-trans thiopropylproline)-Tic-Arg
D-Arg-Arg-Pro-4Hyp-Gly-Phe-Ser-(D-4-trans thiomethylproline)-Oic-Arg
D-Arg-Arg-Pro-4Hyp-Gly-Phe-Ser-(D-4-trans thioethylproline)-Oic-Arg
D-Arg-Arg-Pro-4Hyp-Gly-Phe-Ser-(D-4-trans thiopropylproline)-Oic-Arg
D-Arg-Arg-Pro-4Hyp-Gly-Phe-Ser-(D-4-trans thiomethylproline)-Aoc-Arg
D-Arg-Arg-Pro-4Hyp-Gly-Phe-Ser-(D-4-trans thioethylproline)-Aoc-Arg
D-Arg-Arg-Pro-4Hyp-Gly-Phe-Ser-(D-4-trans thiopropylproline)-Aoc-Arg Thioaryl Ethers and Substituted Aryl Ethers D-Arg-Arg-Pro-4Hyp-Gly-Thi-Ser-(D-4-trans thiophenylproline)-Tic-Arg
D-Arg-Arg-Pro-4Hyp-Gly-Thi-Ser-(D-4-trans thiophenylproline)-Oic-Arg
D-Arg-Arg-Pro-4Hyp-Gly-Thi-Ser-(D-4-trans thiophenylproline)-Aoc-Arg
D-Arg-Arg-Pro-4Hyp-Gly-Phe-Ser-(D-4-trans thiophenylproline)-Tic-Arg
D-Arg-Arg-Pro-4Hyp-Gly-Phe-Ser-(D-4-trans thiophenylproline)-Oic-Arg
D-Arg-Arg-Pro-4Hyp-Gly-Phe-Ser-(D-4-trans thiophenylproline)-Aoc-Arg
D-Arg-Arg-Pro-4Hyp-Gly-Phe-Ser-(D-4-hydroxyproline trans 4'-nitrophenyl ether)-Oic-Arg
D-Arg-Arg-Pro-4Hyp-Gly-Phe-Ser-(D-4-hydroxyproline trans napthal thioether)-Oic-Arg
D-Arg-Arg-Pro-4Hyp-Gly-Phe-Ser-(D-4-hydroxyproline cis phenyl thioether)-Oic-Arg
D-Arg-Arg-Pro-4Hyp-Gly-Phe-Ser-(D-4-hydroxyproline trans 2'-nitrophenyl ether)-Oic-Arg
D-Arg-Arg-Pro-Pro-Gly-Phe-Ser-(D-4-hydroxyproline trans phenyl thioether)-Oic-Arg
D-Arg-Arg-Pro-4Hyp-Gly-Phe-Ser-(D-4-hydroxyproline trans p-chlorophenyl thioether)-Oic-Arg
D-Arg-Arg-Pro-4Hyp-Gly-Phe-Ser-(D-4-hydroxyproline trans p-methylphenyl thioether)-Oic-Arg Allyl Ethers D-Arg-Arg-Pro-4Hyp-Gly-Thi-Ser-(D-4-Hydroxyproline trans allyl ether)-Tic-Arg
D-Arg-Arg-Pro-4Hyp-Gly-Thi-Ser-(D-4-Hydroxyproline trans allyl ether)-Oic-Arg
D-Arg-Arg-Pro-4Hyp-Gly-Thi-Ser-(D-4-Hydroxyproline trans allyl ether)-Aoc-Arg
D-Arg-Arg-Pro-4Hyp-Gly-Phe-Ser-(D-4-Hydroxyproline trans allyl ether)-Tic-Arg D-Arg-Arg-Pro-4Hyp-Gly-Phe-Ser-(D-4-Hydroxyproline trans allyl ether)-Oic-Arg
D-Arg-Arg-Pro-4Hyp-Gly-Phe-Ser-(D-4-Hydroxyproline trans allyl ether)-Aoc-Arg
Hydroxyproline Ethers Hydroxyproline Ethers
D-Arg-Arg-Pro-4Hyp-Gly-Thi-Ser-(D-4-Hydroxyproline trans methyl ether)-(L-4-Hydroxyproline cis methyl ether)-Arg
D-Arg-Arg-Pro-4Hyp-Gly-Thi-Ser-(D-4-Hydroxyproline trans ethyl ether)-(L-4-Hydroxyproline cis methyl ether)-Arg
D-Arg-Arg-Pro-4Hyp-Gly-Thi-Ser-(D-4-Hydroxyproline trans propyl ether)-(L-4-Hydroxyproline cis methyl ether)-Arg
D-Arg-Arg-Pro-4Hyp-Gly-Thi-Ser-(D-4-Hydroxyproline trans methyl ether)-(L-4-Hydroxyproline cis ethyl ether)-Arg
D-Arg-Arg-Pro-4Hyp-Gly-Thi-Ser-(D-4-Hydroxyproline trans ethyl ether)-(L-4-Hydroxyproline cis ethyl ether)-Arg
D-Arg-Arg-Pro-4Hyp-Gly-Thi-Ser-(D-4-Hydroxyproline trans propyl ether)-(L-4-Hydroxyproline cis ethyl ether)-Arg
D-Arg-Arg-Pro-4Hyp-Gly-Thi-Ser-(D-4-Hydroxyproline trans methyl ether)-(L-4-Hydroxyproline cis propyl ether)-Arg
D-Arg-Arg-Pro-4Hyp-Gly-Thi-Ser-(D-4-Hydroxyproline trans ethyl ether)-(L-4-Hydroxyproline cis propyl ether)-Arg
D-Arg-Arg-Pro-4Hyp-Gly-Thi-Ser-(D-4-Hydroxyproline trans propyl ether)-(L-4-Hydroxyproline cis propyl ether)-Arg
D-Arg-Arg-Pro-4Hyp-Gly-Phe-Ser-(D-4-Hydroxyproline trans methyl ether)-(L-4-Hydroxyproline cis methyl ether)-Arg
D-Arg-Arg-Pro-4Hyp-Gly-Phe-Ser-(D-4-Hydroxyproline trans ethyl ether)-(L-4-Hydroxyproline cis methyl ether)-Arg
D-Arg-Arg-Pro-4Hyp-Gly-Phe-Ser-(D-4-Hydroxyproline trans propyl ether)-(L-4-Hydroxyproline cis methyl ether)-Arg
D-Arg-Arg-Pro-4Hyp-Gly-Phe-Ser-(D-4-Hydroxyproline trans methyl ether)-(L-4-Hydroxyproline cis ethyl ether)-Arg
D-Arg-Arg-Pro-4Hyp-Gly-Phe-Ser-(D-4-Hydroxyproline trans ethyl ether)-(L-4-Hydroxyproline cis ethyl ether)-Arg
D-Arg-Arg-Pro-4Hyp-Gly-Phe-Ser-(D-4-Hydroxyproline trans propyl ether)-(L-4-Hydroxyproline cis ethyl ether)-Arg
D-Arg-Arg-Pro-4Hyp-Gly-Phe-Ser-(D-4-Hydroxyproline trans methyl ether)-(L-4-Hydroxyproline cis propyl ether)-Arg
D-Arg-Arg-Pro-4Hyp-Gly-Phe-Ser-(D-4-Hydroxyproline trans ethyl ether)-(L-4-Hydroxyproline cis propyl ether)-Arg
D-Arg-Arg-Pro-4Hyp-Gly-Phe-Ser-(D-4-Hydroxyproline trans propyl ether)-(L-4-Hydroxyproline cis propyl ether)-Arg
D-Arg-Arg-Pro-4Hyp-Gly-Thi-Ser-(D-4-Hydroxyproline trans propyl ether)-(L-4-Hydroxyproline trans methyl ether)-Arg Another embodiment of the invention involves a pharmaceutical composition useful as a bradykinin receptor antagonist comprising a pharmaceutical carrier and an effective amount of the novel bradykinin-type peptide. The invention also involves a process for antagonizing bradykinin receptor activity in mammals which comprises: administering to a subject an effective amount of the novel compound to antagonize bradykinin receptor activity.

A further embodiment involves a pharmaceutical preparation for treating local pain and inflammation from burns, wounds, cuts, rashes and other such trauma, and pathological conditions caused by the production of bradykinin or related kinins by an animal which comprises administering an effective amount of the novel peptide sufficient to antagonize bradykinin with a suitable pharmaceutical carrier. Another aspect of this invention involves a process for treating local pain and inflammation which comprises administering an effective amount of the pharmaceutical preparation to an animal in need thereof.

DETAILED DESCRIPTION OF THE INVENTION

The present compounds which are bradykinin receptor antagonists have the following formula:

N-A-B-C-D-E-F-G-H-I-J-Cn wherein N is hydrogen;
A and B are independently selected from the group consisting of L-Arg, D-Arg, D-Gln, L-Gln, D-Asn, L-Asn, NϵE-acetyl-D-lysine, ϵ-acetyl-L-lysine, $N^G$-p-tosyl-Arg, $N^G$-nitro-Arg, Lys—Lys, acetyl-D-Arg, L-Citrulline, L-Lys, Sar, and D-Lys;
C and D are a direct bond or are independently selected from the group consisting of Pro, dehydroPro, 4Hyp, Tic, Aoc, Ala, L-azetidine-2-carboxylic acid, Eac, Gly, Thz, Oic, and Aib;
E is a direct bond or is selected from the group consisting of Gly, Ala, Thr, and Ser;
F is selected from the group consisting of Phe, Thi, Leu, Ile, Tic, Oic, homoPhe, phenylGly, β-cyclohexylalanine Nal, and Val;
G is a direct bond or is selected from the group consisting of Ser, Thr, 4Hyp, Gly, Val, and Ala;
H is a compound of the D-configuration having the formula:

R—X wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1$NHC(o)— where $R^1$ is $C_1$–$C_6$ alkyl or aryl, and where X is either $SO_n$ or oxygen, and n=0, 1, or 2;
I is selected from the group consisting of Oic, Aoc, Thz, Tic, L-indoline-2-carboxylic acid, octahydro-1H-isoindole-1-carboxylic acid, pipecolinic acid, Pro, 4Hyp, azetidine-2-carboxylic acid, Aib, Leu, Ile, Val, Thi, Phe, homoPhe, and compounds of the formula:

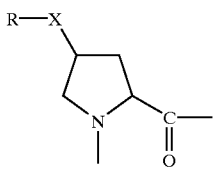

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either $SO_n$ or oxygen, and n=0, 1, or 2;

J is selected from the group consisting of Arg, Orn, Asn, Gln, N-ε-acetyl-Lys, N-δ-acetyl-Orn, and Lys;

Cn is a hydroxyl group a C-terminal extension selected from the group consisting of amide, alkoxy group, an acidic, basic or neutral aliphatic aromatic, and cyclic amino acid residue of the D- or L-configuration, and a peptide extension composed of D- or L-amino acids; and pharmaceutically acceptable salts thereof.

Formula 2

Preferred compounds are those in which:

N is hydrogen;

A and B are independently selected from the group consisting of L-Arg, D-Arg, Lys—Lys, Lys;

C and D are independently selected from the group consisting of Pro, dehydroPro, and 4Hyp;

E is Gly;

F is selected from the group consisting of Phe, Thi, Leu, and β-cyclohexylalanine;

G is a direct bond or is selected from the group consisting of Ser and Thr;

H is a compound of the D-configuration having the formula:

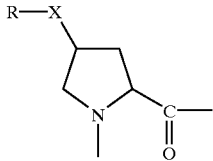

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either $SO_n$ or oxygen, and n=0, 1, or 2;

I is selected from the group consisting of Oic, Aoc, Thz, Pro, pipecolinic acid, Leu, Phe, Thi, Tic, and compounds of the formula:

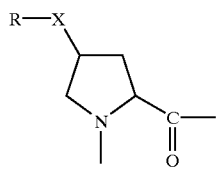

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either $SO_n$ or oxygen, and n=0, 1, or 2;

J is selected from the group consisting of Arg and Lys;

Cn is hydroxyl;

and pharmaceutically acceptably salts thereof.

Formula 3

Most preferred are compounds wherein:

N is hydrogen;

A is D-Arg;

B is Arg;

C is Pro;

D is selected from the group consisting of Pro and 4Hyp;

E is Gly;

F is selected from the group consisting of Phe, Leu, and Thi; G is a direct bond or is Ser;

H is a compound of the D-configuration having the formula:

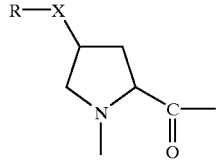

wherein R is selected from the group consisting of methyl, ethyl, propyl, isobutyl, cyclohexylmethyl, allyl, methallyl, prenyl, benzyl, phenyl, nitrophenyl, napthal, chlorophenyl, methylphenyl, phenylpropyl, and methylbutyl, and where X is either $SO_n$ or oxygen, and n=0, 1, or 2;

I is selected from the group consisting of Oic, Aoc, Thz, Tic, and compounds of the formula:

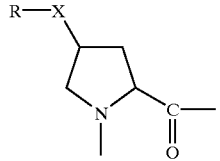

wherein R is selected from the group consisting of methyl, ethyl, propyl, isobutyl, cyclohexylmethyl, allyl, methallyl, prenyl, benzyl, phenyl, and phenylcarbamoyl, and where X is either $SO_n$ or oxygen, and n=0, 1, or 2;

J is Arg;

Cn is a hydroxyl group;

and pharmaceutically acceptable salts thereof.

Formula 4

The inventive compositions also include the following preferred formulations:

A is D-Arg;
B is Arg;
C and D are independently selected from the group consisting of Pro and 4Hyp;
E is Gly;
F is Phe;
G is Ser;
H is a compound of the D-configuration having the formula:

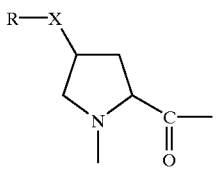

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1$NHC(o)— where $R^1$ is $C_1$–$C_6$ alkyl or aryl, and where X is either $SO_n$ or oxygen, and n=0, 1, or 2;
I is selected from the group consisting of Tic, Aoc, and Oic;
J is Arg;
CN is a hydroxyl group;
and pharmaceutically acceptable salts thereof.

Formula 5

A is D-Arg;
B is Arg;
C and D are independently selected from the group consisting of Pro and 4Hyp;
E is Gly;
F is selected from the group consisting of Phe and Thi;
G is Ser;
H is a compound of the D-configuration having the formula:

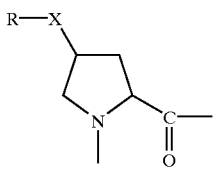

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1$NHC(o)— where $R^1$ is $C_1$–$C_6$ alkyl or aryl, and where X is either $SO_n$ or oxygen, and n=0, 1, or 2;
I is Oic;
J is Arg;
CN is a hydroxyl group;
and pharmaceutically acceptable salts thereof.

Formula 6

A is D-Arg;
B is Arg;
C and D are independently selected from the group consisting of Pro and 4Hyp;
E is Gly;
F is Phe;
G is Ser;
H is a compound of the D-configuration having the formula:

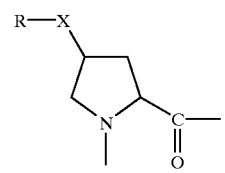

wherein R is selected from the group consisting of methyl, ethyl, propyl, phenyl, chlorophenyl, naphthyl, methylphenyl, and X is sulfur;
I is Oic;
J is Arg;
and pharmaceutically acceptable salts thereof.

Formula 7

A is D-Arg;
B is Arg;
C and D are independently selected from the group consisting of Pro and 4Hyp;
E is Gly;
F is Phe;
G is Ser;
H is a compound of the D-configuration having the formula:

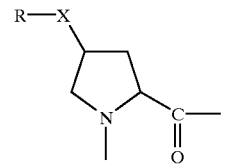

wherein R is selected from the group consisting of methyl, ethyl, propyl, 3-phenylpropyl, methylbutyl, and phenyl and X is oxygen;
I is Oic;
J is Arg;
and pharmaceutically acceptable salts thereof.

Formula 8

A is D-Arg;
B is Arg;
C and D are independently selected from the group consisting of Pro and 4Hyp;
E is Gly;
F is selected from the group consisting of Phe and Thi;
G is a direct bond or is Ser;
H is a compound of the D-configuration having the formula:

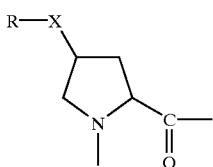

wherein R is selected from the group consisting of methyl, ethyl, propyl, chlorophenyl, methylphenyl, phenylpropyl, and phenyl and X is sulfur or oxygen;

I is Oic;

J is Arg;

and pharmaceutically acceptable salts thereof.

Formula 9

A is D-Arg;

B is Arg;

C and D are independently selected from the group consisting of Pro and 4Hyp;

E is Gly;

F is Phe;

G is Ser;

H is a compound of the D-configuration having the formula:

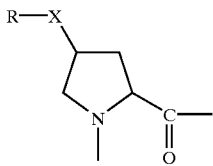

wherein R is methyl and X is oxygen;

I is Oic;

J is Arg;

and pharmaceutically acceptable salts thereof.

Formula 10

A is D-Arg;

B is Arg;

C and D are independently selected from the group consisting of Pro and 4Hyp;

E is Gly;

F is Phe;

G is Ser;

H is a compound of the D-configuration having the formula:

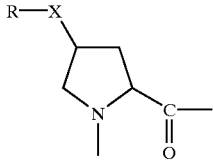

wherein R is ethyl and X is oxygen;

I is Oic;

J is Arg;

and pharmaceutically acceptable salts thereof.

Formula 11

A is D-Arg;

B is Arg;

C and D are independently selected from the group consisting of Pro and 4Hyp;

E is Gly;

F is Phe;

G is Ser;

H is a compound of the D-configuration having the formula:

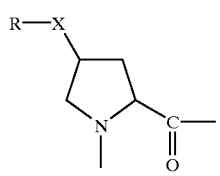

wherein R is propyl and X is oxygen;

I is Oic;

J is Arg;

and pharmaceutically acceptable salts thereof.

Formula 12

A is D-Arg;

B is Arg;

C and D are independently selected from the group consisting of Pro and 4Hyp;

E is Gly;

F is Phe;

G is Ser;

H is a compound of the D-configuration having the formula:

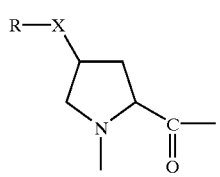

wherein R is phenyl and X is oxygen;

I is Oic;

J is Arg;

and pharmaceutically acceptable salts thereof.

Formula 13

A is D-Arg;

B is Arg;

C and D are independently selected from the group consisting of Pro and 4Hyp;

E is Gly;

F is Phe;

G is Ser;

H is a compound of the D-configuration having the formula:

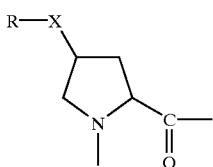

wherein R is allyl and X is oxygen;
I is Oic;
J is Arg;
and pharmaceutically acceptable salts thereof.
Formula 14
A is D-Arg;
B is Arg;
C and D are independently selected from the group consisting of Pro and 4Hyp;
E is Gly;
F is selected from the group consisting of Thi and Phe;
G is Ser;
H is a compound of the D-configuration having the formula:

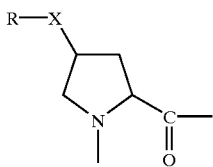

wherein R is 3-methylbutyl and X is oxygen;
I is Oic;
J is Arg;
and pharmaceutically acceptable salts thereof.
Formula 15
A is D-Arg;
B is Arg;
C and D are independently selected from the group consisting of Pro and 4Hyp;
E is Gly;
F is selected from the group consisting of Thi and Phe;
G is Ser;
H is a compound of the D-configuration having the formula:

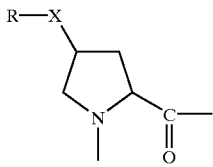

wherein R is 3-phenylpropyl and X is oxygen;
I is Oic;
J is Arg;
and pharmaceutically acceptable salts thereof.
Formula 16
A is D-Arg;
B is Arg;
C and D are independently selected from the group consisting of Pro and 4Hyp;
E is Gly;
F is Phe;
G is Ser;
H is a compound of the D-configuration having the formula:

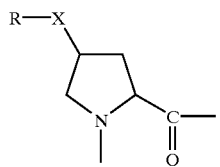

wherein R is methyl and X is sulfur;
I is Oic;
J is Arg;
and pharmaceutically acceptable salts thereof.
Formula 17
A is D-Arg;
B is Arg;
C and D are independently selected from the group consisting of Pro and 4Hyp;
E is Gly;
F is Phe;
G is Ser;
H is a compound of the D-configuration having the formula:

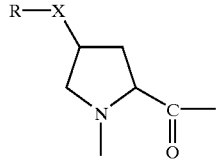

wherein R is ethyl and X is sulfur;
I is Oic;
J is Arg;
and pharmaceutically acceptable salts thereof.
Formula 18
A is D-Arg;
B is Arg;
C and D are independently selected from the group consisting of Pro and 4Hyp;
E is Gly;
F is Phe;
G is Ser;
H is a compound of the D-configuration having the formula:

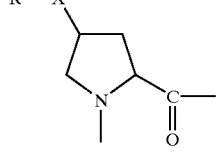

wherein R is propyl and X is sulfur;
I is Oic;
J is Arg;

and pharmaceutically acceptable salts thereof.

Formula 19

A is D-Arg;

B is Arg;;

C and D are independently selected from the group consisting of Pro and 4Hyp;

E is Gly;

F is selected from the group consisting of Thi and Phe;

G is Ser;

H is a compound of the D-configuration having the formula:

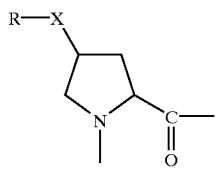

wherein R is phenyl and X is sulfur;

I is Oic;

J is Arg;

and pharmaceutically acceptable salts thereof.

Formula 20

A is D-Arg;

B is Arg;

C and D are independently selected from the group consisting of Pro and 4Hyp;

E is Gly;

F is selected from the group consisting of Thi and Phe;

G is Ser;

H is a compound of the D-configuration having the formula:

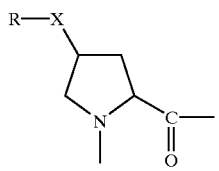

wherein R is p-chlorophenyl and X is sulfur;

I is Oic;

J is Arg;

and pharmaceutically acceptable salts thereof.

Formula 21

A is D-Arg;

B is Arg;

C and D are independently selected from the group consisting of Pro and 4Hyp;

E is Gly;

F is selected from the group consisting of Thi and Phe;

G is Ser;

H is a compound of the D-configuration having the formula:

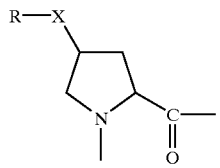

wherein R is p-methylphenyl and X is sulfur;

I is Oic;

J is Arg;

and pharmaceutically acceptable salts thereof.

Formula 22

A is D-Arg;

B is Arg;

C and D are independently selected from the group consisting of Pro and 4Hyp;

E is Gly;

F is Phe;

G is Ser;

H is a compound of the D-configuration having the formula:

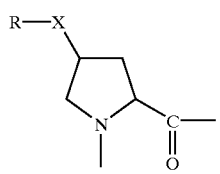

wherein R is selected from the group consisting of methyl, ethyl, propyl, allyl, methallyl, benzyl, phenyl, nitrophenyl, napthal, chlorophenyl, methylphenyl, phenylpropyl, methylbutyl and phenyl, and where X is either $SO_n$ or oxygen, and n=0, 1, or 2;

I is a compound of the formula:

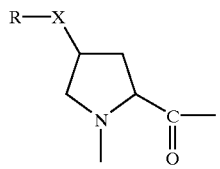

wherein R is selected from the group consisting of methyl, ethyl, propyl, allyl, methallyl, benzyl, methylphenyl, chlorophenyl, phenylpropyl, and phenyl and where X is either $SO_n$ or oxygen, and n=0, 1, or 2;

J is Arg;

and pharmaceutically acceptable salt thereof.

The invention also contemplates the preparation of an intermediate chemical entity as well as its use to prepare a bradykinin antagonist peptide. The intermediate is in the D-configuration, either the cis or trans structure, preferably trans has formula:

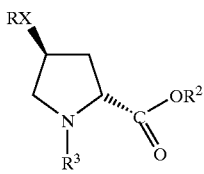

wherein R is selected from the group consisting of, hydrogen, $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either $SO_n$ or oxygen, and n=0, 1, or 2;

R2 is selected from the group consisting of hydrogen, C1–$C_6$ alkyl, $C_2$–$C_8$ alkenyl, an aryl group, and an arylalkyl group;

$R^3$ is H or a suitable amine protecting group; provided that when R is hydrogen, $R^2$ is a $C_1$–$C_6$ alkyl group.

As used in the specification and claims, "alkyl" is a paraffinic hydrocarbon group which may be derived from an alkane by dropping one hydrogen from the formula, such as methyl, ethyl, propyl, isopropyl, butyl, and so forth; "substituted $C_1$–$C_6$ alkyl" is a branched alkyl, such as methyl butyl; "aryl" is an aromatic ring compound such as benzene, phenyl, naphthyl; "substituted aryl" is a substituted aromatic ring, such as nitro substitution, or halogen substitution; and "aralkyl" is an aryl being attached through an alkyl chain, straight or branched, containing from one through six carbons, such as a phenylpropyl group. A "direct bond" is a bond which replaces a particular amino acid compound between adjacent amino acids and which amino acid may also be indicated to be absent by the term "null". The phrase "a suitable amine protecting group" is a group, such as BOC (t-butyloxy-carbonyl-) protecting group which protects the amine moiety from reaction and which can be removed under mild conditions so as not to affect the rest of the molecule.

Exemplary Boc protected amino acids include the following nonlimiting materials:
N-Boc-L-cis-4-methoxyproline;
N-Boc-L-cis-4-(n-propoxy)proline;
N-Boc-L-trans-4-methoxyproline;
N-Boc-L-trans-4-(n-propoxy)proline;
N-Boc-L-trans-4-ethoxyproline;
N-Boc-D-trans-4-phenylthioproline;
N-Boc-D-trans-4-methoxyproline;
N-Boc-L-trans-4-cyclohexylmethoxyproline;
N-Boc-D-trans-4-(3-methylbutoxy)proline;
N-Boc-D-trans-4-(3-phenylpropoxy)proline;
N-Boc-D-trans-4-(p-chlorophenylthio)proline;
N-Boc-D-trans-4-(2-naphthalenethio)proline;
N-Boc-D-trans-4-hydroxyproline methyl ester;
N-Boc-D-trans-4-(n-propoxy)proline;
N-Boc-D-trans-4-ethoxyproline;
N-Boc-L-trans-4-phenylthioproline;
N-Boc-L-trans-4-phenoxyproline;
N-Boc-D-trans-4-(2-nitrophenoxy)proline;
N-Boc-D-cis-4-phenylthioproline;
N-Boc-D-trans-4-(4-nitrophenoxy)proline.
N-Boc-L-trans-4-ethoxyproline
N-Boc-D-trans-4-(p-methylphenylthio)proline
N-Boc-L-cis-4-ethoxyproline
N-Boc-L-trans-4-O-phenylcarbamoylproline Definitions of the amino acid abbreviations used herein are as follows:

Arg is arginine; Ala is alanine; Aib is 2-aminoisobutyric acid; Aoc is (S,S,S)-2-azabicyclo[3.3.0]octane-3-carboxylic acid; Asn is asparagine; Eac is ε-aminocaproic acid; Gln is glutamine; Gly is glycine; Ile is isoleucine; Leu is leucine; Lys is lysine; Met is methionine; Nal is beta-2-naphthylalanine; Orn is ornithine; Pro is proline; dehydroPro is 3,4-dehydroproline; homoPhe is homophenylalanine; 4Hyp is 4-hydroxyproline; Ser is serine; Sar is sarcosine; Thi is beta-2-thienylalanine; Thr is threonine; Thz is thiazolidine-4-carboxylic acid; Phe is phenylalanine; phenylGly is 2-phenylglycine; Tic is tetrahydroisoquinoline-3-carboxylic acid; Oic is (2S, 3aS, 7aS)-octahydro-1H-indole-2-carboxylic acid; Val is valine. Further more, prenyl is a 3-methyl-2-butenyl radical.

Aoc can be prepared by the method of V. Teetz, R. Geiger and H. Gaul, Tetrahedron Lett. (1984), 4479. Tic can be prepared by the method of K. Hayashi, Y. Ozaki, K. Nunami and N. Yoneda, Chem. Pharm. Bull. (1983) 31, 312.

All amino acids residues, except Gly, and Sar, described in the specification are preferably of the L-configuration unless otherwise specified. It would be recognized, however, that the 7 position must always be the D-configuration whereas the hydroxyproline ethers and thioethers of position 8 may be either in the D- or L-configuration. The symbols and abbreviations used for amino acids, their derivatives and protecting groups, and peptides and their salts are those customarily used in peptide chemistry. (See Biochem. J. (1972), 126, 773), which Journal reference is hereby incorporated by reference).

Table I shows the general location of the amino acid groups as used herein.

TABLE I

| N – A – B – C – D – E – F – G – H – I – J – Cn | (formula) |
|---|---|
| Arg-Pro-Pro-Gly-Phe-Ser-Pro-Phe-Arg | Bradykinin |
| 1   2   3   4   5   6   7   8   9 | (position number) |

The synthesis of the peptides of this invention including derivation, activation, and coupling of protected amino acid residues, and their purification, and the analytical methods for determining identity and purity are included in the general body of knowledge of peptide chemistry, as described in Houben Weyl Methoden der Organischen Chemie, (1974), Vol. 16, parts I & II for solution-phase synthesis, and in Solid Phase Peptide Synthesis, (1984), by Stewart and Young for synthesis by the solid-phase method of Merrifield.

Any chemist skilled in the art of peptide synthesis can synthesize the peptides of this invention by standard solution methods or by manual or automated solid phase methods.

The appropriate hydroxyproline substituents used in the 7-position are prepared by the process described in the Examples and depicted in the sequences shown below. The starting materials are commercially available and can be prepared by known procedures. Both the cis and trans stereoisomers can be prepared by these means and are within the scope of the present invention.

In Scheme II M represents sodium, potassium and other useable salts such as alkaline earth metals and alkali metals and X is oxygen or sulfur.

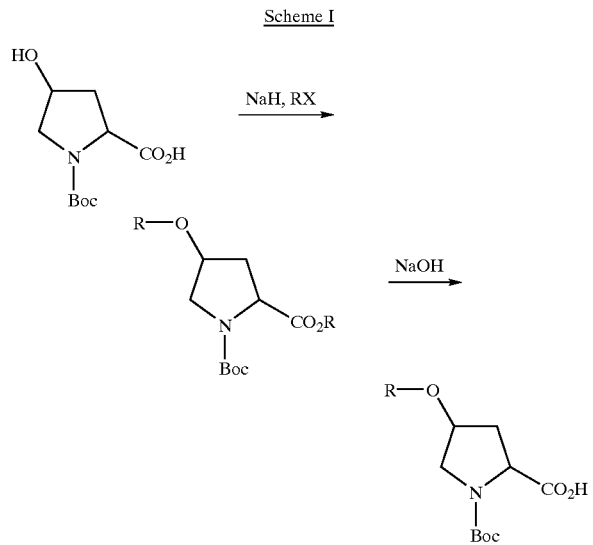

Scheme I

Alternately, they also can be prepared by the method of Scheme II from commercially available starting materials.

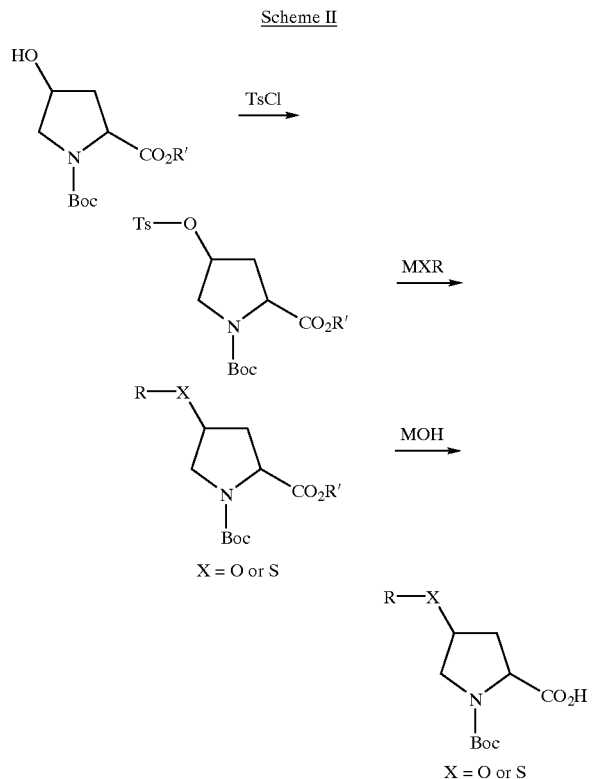

Scheme II

The preparation of compounds for administration in pharmaceutical preparations may be performed in a variety of methods well known to those skilled in the art. Appropriate pharmaceutically acceptable salts within the scope of the invention are those derived from mineral acids such as hydrochloric acid, hydrobromic acid, phosphoric acid, nitric acid and sulfuric acid; and organic acids such as tartaric acid, fumaric acid, lactic acid, oxalic acid, ethylsulfonic acid, citric acid, methanesulfonic acid, benzenesulfonic acid, p-toluenesulfonic acid, and the like, giving the hydrochloride, sulfate, phosphate, nitrate, methanesulfonate, tartrate, benzenesulfonate, p-toluensulfonate, and the like, salt, respectively.

The compounds of the invention may contain an asymmetric carbon atom. Thus, the invention includes the individual stereoisomers, and the mixtures thereof. The individual isomers may be prepared or isolated by methods known in the art.

Therapeutic applications of the novel bradykinin antagonists include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic inflammatory or pathological conditions which are known to be mediated by bradykinin or exacerbated by an overproduction of bradykinin can also be achieved. These conditions include local trauma such as wounds, burns and rashes, angina, arthritis, asthma, allergies, rhinitis, shock, inflammatory bowel disease, low blood pressure, and systemic treatment of pain and inflammation.

In parenteral administration of the novel compounds and compositions of the invention the compounds may be formulated in aqueous injection solutions which may contain antioxidants, buffers, bacteriostats, etc. Extemporaneous injection solutions may be prepared from sterile pills, granules or tablets which may contain diluents, dispersing and surface active agents, binders and lubricants which materials are all well known to the ordinary skilled artisan.

In the case of oral administration, fine powders or granules of the compound may be formulated with diluents and dispersing and surface active agents, and may be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening, and emulsifying agents. The granules or tablets for oral administration may be coated and other pharmaceutically acceptable agents and formulations may be utilized which are all known to those skilled in the pharmaceutical art.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs suitably are prepared using known polymeric materials such as various acrylic-based polymers selected to provide desired release characteristics. Suppositories are prepared from standard bases such as polyethylene glycol and cocoa butter.

The method of treatment according to this invention comprises administering internally or topically to a subject an effective amount of the active compound. Doses of active compounds in the inventive method and pharmaceutical compositions containing same are an efficacious, nontoxic quantity selected from the range of 0.01 to 100 mg/kg of active compound, preferably 0.1 to 50 mg/kg. Persons skilled in the art using routine clinical testing are able to determine optimum doses for the particular ailment being treated. The desired dose is administered to a subject from 1 to 6 or more times daily, orally, rectally, parenterally, topically, or by inhalation.

The efficacy of the inventive compounds of this invention as bradykinin receptor antagonists can be determined using the bradykinin binding and tissue assays described herein. The results of these assays demonstrate that the novel compounds are potent, selective bradykinin receptor antagonists.

The following examples are illustrative of preferred embodiments of methods of preparation and compounds of the invention and are not to be construed as limiting the invention thereto.

EXAMPLE 1

This Example demonstrates the preparation of N-Boc-L-cis-4-methoxyproline by Scheme I.

To a stirred suspension of sodium hydride (3.38 g, 80%, 112 mmole) [washed with hexanes, 2×20 mL] in anhydrous dimethylformamide (60 mL) was added dropwise a solution of N-Boc-L-cis-4-hydroxyproline (10.0 g, 43.0 mmole) in anhydrous dimethylformamide (60 mL) at room temperature (22° C.) under argon. After 30 min, the suspension was treated with iodomethane (20.0 g, 146 mmole) and the resultant mixture was stirred at room temperature for 24 hours. Water (100 mL) and aqueous hydrochloric acid (1N) were added until the solution was acidic to Congo red indicator. The aqueous solution was extracted with diethyl ether (3×250 mL), the combined extracts dried over sodium sulfate, and concentrated to an oil. The crude product was used directly in the next step without purification.

To a stirred solution of the crude product in methanol (30 mL) was added aqueous sodium hydroxide (25 mL, 3 N, 75 mmol) at room temperature (22° C.). After 18 hours, the reaction mixture was diluted with water (35 mL) and concentrated hydrochloric acid was added to adjust the mixture to pH 10. The mixture was extracted with diethyl ether (3×55 mL) and the organic layer was discarded. The aqueous layer was further acidified to the Congo red indicator endpoint and extracted with ethyl acetate (2×250 mL, 1×100 mL). Drying with sodium sulfate and concentration gave an oil. Addition of hexane caused precipitation of the product. The solids were collected, washed with 50% ethyl acetate in hexane (20 mL), and dried in vacuo at room temperature to afford the desired product (7.75 g, overall yield 73.3%): mp 119.5–121.8° C.

EXAMPLE 2

This Example demonstrates the preparation of N-Boc-L-cis-4-(n-propoxy)proline according to Scheme I with an additional hydrogenation step.

To a stirred suspension of sodium hydride (2.86 g, 80%, 95.5 mmole) [washed with anhydrous hexane (2×20 mL)] in anhydrous dimethylformamide (60 mL) was added dropwise a solution of N-Boc-L-cis-4-hydroxyproline (8.80 g, 37.8 mmole) in anhydrous dimethylformamide (60 mL) at room temperature (22° C.) under argon. After 30 min., a solution of allyl bromide (11.46 g, 94.7 mmole) in anhydrous dimethylformamide (35 mL) was added dropwise at room temperature. After 24 hours, water (100 mL) was added followed by aqueous hydrochloric acid (1 N) until the mixture was acidic (pH 3). The aqueous solution was extracted with diethyl ether (3×160 mL), the combined extracts were dried over sodium sulfate, and concentrated to an oil. The crude product was used directly in the next step without purification.

To a stirred solution of the crude product in methanol (30 mL) was added a solution of aqueous sodium hydroxide (3 N, 25 mL, 75 mmol) at room temperature. After 18 hours, the reaction mixture was diluted with water (35 mL) and concentrated hydrochloric acid was added to adjust the solution to pH 10. The solution was washed with diethyl ether (2×55 mL) and the combined organics were discarded. The aqueous layer was acidified to the Congo red indicator endpoint and extracted with ethyl acetate (3×180 mL). The combined organics were dried over sodium sulfate and concentrated to an oil (9.60 g).

A suspension of above product and 5% platinum on activated carbon (0.74 g) in ethyl acetate (100 mL) was shaken under 35 psi of hydrogen at room temperature. After 6.5 hours, the catalyst was removed and washed with ethyl acetate. Concentration and flash chromatography (silica gel, 20% methanol in methylene chloride) gave the desired product (8.49 g, overall yield 86.2%) as an oil: IR (neat film) cm-1 3500-2550 (broad), 2972, 2933, 2877, 1748, 1707, 1478, 1400, 1367, 1164, 1100, 1007, 900, 856; 1H NMR (300 MHz, CDCl3) ppm 0.89 (t, 3H, J=7.2 Hz), 1.45 (2 x s, 9H), 1.55 (q, 2H, J=7.2 Hz), 2.21 (m, 2H), 3.40 (m, 2H), 4.04 (t, 1H, J=3.3 Hz), 4.43 (m, 1H), 8.80 (s, 1H).

EXAMPLE 3

This Example demonstrates the preparation of (2S,4R)-N-(tert-Butoxycarbonyl)-4-O-(phenylcarbamoyl)proline.

To a stirred solution of N-Boc-L-trans-hydroxyproline methyl ester (4.05 g, 16.5 mmol) and 4-dimethylaminopyridine (0.11 g, 0.89 mmol) in CHCl$_3$ (30 mL) was added phenyl isocyanate (1.82 mL, 16.7 mmol) at room temperature. After 21 hours, the mixture was washed with aqueous HCl (10 mL, 0.5 N) and dried (MgSO$_4$). Concentration and drying in vacuo gave (2S, 4R)-N-Boc-4-O-(phenylcarbamoyl)proline methyl ester (6.00 g, 100%) as white solids: mp 129–131° C.

To a stirred suspension of this ester (5.00 g, 14.4 mmol) in MeOH (20 mL) and water (5 mL) was added aqueous NaOH (5.0 mL, 3 N, 15 mmol). After 20 hours at room temperature, additional aqueous NaOH (1.0 mL, 3 N, 3.0 mmol) was added. After an additional 4 hours, the mixture was extracted with EtOAc (3×30 mL). The organics were discarded and the aqueous layer was acidified to the Congo red indicator endpoint with concentrated HCl at 5° C. The mixture was saturated with NaCl and extracted with EtOAc (4×50 mL). The combined organics were dried (Na$_2$SO$_4$) and concentrated to give white solids which were purified by flash chromatography (silica gel, 90:10:1 CH$_2$Cl$_2$:MeOh:HOAc) to afford the desired product (3.66 g, 76%) as white solids: mp 161–163° C.; IR (KBr) cm$^{-1}$ 3430, 3247, 1730, 1686, 1607, 1550, 1445, 1419, 1226, 1159, 1069, 753; $^1$H NMR (300 MHz, CDCl$_3$) δ 1.44% 1.47 (2 x s, 9H), 2.38 (m, 1H), 2.49 (m, 1H), 3.70 (m, 2H), 4.41 (m, 1H), 5.33 (m, 1H), 7.07 (m, 2H), 7.30 (m, 3H), 7.38 (br s, 1H), 9.67 (br s, 1H); [α]$^{22.5}{}_D$=−38.9 (c=1.05, MeOH). Anal. Calcd for C$_{17}$H$_{22}$N$_2$O$_6$.075 H$_2$O (363.88 g/mol): C, 56.11; H, 6.51; N, 7.70. Found: C, 56.20 & 56.13; H, 6.49 & 6.51; N, 7.75.

EXAMPLE 4

This Example demonstrates the preparation of N-Boc-L-trans-4-(n-propoxy)proline according to Scheme I with an additional hydrogenation step.

To a stirred suspension of sodium hydride (1.68 g, 80%, 56.0 mmole) [washed with anhydrous hexane, (2×20 mL)] in anhydrous dimethylformamide (30 mL) was added dropwise a solution of N-Boc-L-trans-4-hydroxyproline (5.0 g, 21.5 mmole) in anhydrous dimethylformamide (35 mL) at room temperature (22° C.) under argon. After 30 min, a solution of allyl bromide (5.73 g, 47.4 mmole) in anhydrous dimethylformamide (35 mL) was added dropwise at room temperature. After 24 hours, the mixture was diluted with water (10 mL) and acidified with aqueous hydrochloric acid (5 N) to pH 3. The aqueous solution was extracted with diethyl ether (2×75 mL), and with ethyl acetate (2×75 mL). The combined extracts were washed with water (2×100 mL), with brine (70 mL), and dried over sodium sulfate. Concentration gave an oil. The crude product was used directly in the next step without purification.

A suspension of the crude product (6.0 g) and 5% platinum on activated carbon (0.97 g) in ethyl acetate (65 mL) was shaken under 35 psi of hydrogen at room temperature (22° C.). After 6.5 hours, the catalyst was removed and washed with ethyl acetate. Concentration and flash chromatography (silica gel, gradient elution with ethyl acetate in hexane (1:1) to ethyl acetate) gave N-Boc-L-trans-4-(n-propoxy)proline propyl ether propyl ester (2.90 g) as an oil.

To a stirred solution of N-Boc-L-trans-4-(n-propoxy) proline propyl ester (2.90 g, 9.16 mmole) in ethanol (10 mL) was added aqueous sodium hydroxide (12 mL, 3 N, 36 mmol) at room temperature. After 4 hours, the reaction mixture was acidified to the Congo red indicator endpoint with aqueous hydrochloric acid (3 N), the reaction mixture was saturated with sodium chloride, and extracted with diethyl ether (4×45 mL). The combined organics were dried over sodium sulfate and concentrated to an oil. Flash chromatography (silica gel, methylene chloride:methanol:acetic acid 90:8:2) gave the desired product (2.50 g, overall yield 42.5%) as an oil: 1H NMR (300 MHz, CDCl3) ppm 0.91(t, 3H, J=7.5 Hz); 1.45 (2 x s, 9H), 1.56 (m, 2H), 2, 28 (t, 1H, J=6.6 Hz), 2.37 (m, 1H), 3.40 (m, 2H), 3.55 (m, 2H), 4.06 (q, 1H, J=4.5 Hz), 4.38 (m, 1H), 10.54 (s, 1H).

EXAMPLE 5

This Example demonstrates the preparation of N-Boc-L-trans-4-methoxyproline.

To a stirred suspension of sodium hydride (1.43 g, 80%, 47.7 mmol) [washed twice with hexanes] in a mixture of anhydrous N,N-dimethylformamide (15 mL) and anhydrous tetrahydrofuran (40 mL) at 5° C. under argon was added N-Boc-L-trans-4-hydroxyproline (5.00 g, 21.6 mmol). When the gas evolution had subsided (ca. 10 min), iodomethane (3.40 mL, 54.1 mmol) was added at 5° C. After 24 hours at room temperature, the suspension was diluted with water (30 mL) and acidified to the Congo red indicator endpoint with aqueous hydrochloric acid (1N) and extracted with ethyl acetate (4×100 mL). The combined organics were washed with aqueous sodium thiosulfate, with water, with brine, and dried (magnesium sulfate). Concentration gave a yellow oil which was used in the next step without purification.

To a stirred solution of the oil in water (25 mL) and 2-propanol (8 mL) was added aqueous potassium hydroxide (16.5 mL, 2.0 N, 33 mmol). After 5 days at room temperature, the mixture was diluted with water (10 mL) and extracted with diethyl ether (2×50 mL). The combined organics were back-extracted with half-saturated aqueous potassium bicarbonate (20 mL) and discarded. The combined aqueous layers were cooled at 5° C., acidified to pH 4 with citric acid, saturated with sodium chloride, and extracted with ethyl acetate (4×50 mL). The combined ethyl acetate extracts were dried (sodium sulfate) and concentrated to an oil. Flash chromatography (silica gel, 91:8:1 chloroform:methanol:acetic acid) followed by extensive drying in vacuo gave the desired product as a slightly yellow syrup (4.90 g, 92% overall): IR (KBr) cm$^{-1}$ 2977, 2933, 1746 (sh), 1697, 1417, 1368, 1254, 1162, 1098; $^1$H NMR (300 MHz, CDCl$_3$) ppm 1.42 & 1.47 (2 x s, 9H total), 2.10 (m, 1H), 2.24 (m, 1H), 3.33 (s, 3H), 3.60 (m, 2H), 4.00 (m, 1H), 4.30 & 4.42 (2 x m, 1H total), 10.27 (br s, 1H).

Dicyclohexylammonium salt (recrystallized from n-heptane): mp 126–128° C.; $[\alpha]^{22.5}_D$=−30.5 (c=1.02, methanol). Anal. Calcd for $C_{23}H_{42}N_2O_5$ (426.60 g/mol): C, 64.76; H, 9.92; N, 6.57. Found: C, 64.68; H, 9.96; N, 6.53.

Cyclohexylammonium salt (recrystallized from ethyl acetate): mp 155–158° C.; $[\alpha]^{22.5}_D$=−38.7 (c=1.01, methanol). Anal, Calcd for $C_{17}H_{32}N_2O_5$ (344.45 g/mol): C, 59.28; H, 9.36; N, 8.13. Found: C, 59.02; H, 9.38; N, 8.09.

EXAMPLE 6

This Example demonstrates the preparation of N-Boc-D-trans-4-phenylthioproline according to Scheme II.

To a stirred suspension of hexane washed sodium hydride (3.06 g, 80%, 38.1 mmol) in anhydrous tetrahydrofuran (95 mL) was added dropwise thiophenol (4.50 mL, 43.7 mmol) at room temperature (22° C.) under argon. After 1 hour, the mixture was treated with N-Boc-D-cis-4-(p-toluenesulfonyloxy)proline (5.00 g, 12.5 mmol) at room temperature. The resultant mixture was heated under reflux for 8 hours. After cooling to room temperature, the mixture was acidified to the Congo red indicator endpoint with aqueous hydrochloric acid. The solution was extracted with ethyl acetate (4×80 mL) and the combined extracts were dried over sodium sulfate. Concentration gave an oil which was used directly in the next step without purification.

To a stirred solution of the crude N-Boc-D-trans-4-phenylthioproline methyl ester in methanol (20 mL) at room temperature was added a solution of sodium hydroxide (18 mL, 3N). After two days at room temperature, water (30 mL) was added and the mixture was extracted with diethyl ether (3×45 mL). The combined organics were discarded and the aqueous layer was acidified with aqueous hydrochloric acid (5 N) to the Congo red indicator endpoint. The aqueous layer was extracted with ethyl acetate (3×110 mL) and the combined extracts were dried over sodium sulfate. Concentration followed by flash chromatography (silica gel, methylene chloride/methanol/acetic acid 90:8:2) gave N-Boc-D-trans-4-phenylthioproline (3.64 g, 79.3%) as an oil: IR (neat film) cm$^{-1}$ 3300-2500, 1749, 1702, 1583 (w), 1415, 1398, 1368, 1164, 743; $^1$H NMR (300 MHz, CDCl$_3$) ppm 1.45 & 1.48 (2 x s, 9H), 2.31 (m, 1H), 3.44 (m, 1H), 3.76 (m, 2H), 4.43 (m, 1H), 7.37 (m, 3H), 7.42 (m, 2H), 9.77 (s, 1H).

EXAMPLE 7

This Examples demonstrates the preparation of N-Boc-D-trans-4-(n-propoxy)proline.

To a stirred suspension of sodium hydride (2.04 g, 80%, 68.0 mmol) [washed with anhydrous hexane (2×15 mL)] in anhydrous dimethylformamide (60 mL) was added a solution of N-Boc-D-trans-4-hydroxyproline (6.05 g, 26.1 mmol) in anhydrous dimethylformamide (30 mL) at room temperature (22° C.) under argon. After 30 min., the mixture was treated with allyl bromide (7.91 g, 65.4 mmol). After 21 hours, water (50 mL) was added followed by aqueous hydrochloric acid (5N) to the Congo red indicator endpoint and the mixture was extracted with diethyl ether (3×130 mL). The combined extracts were dried over sodium sulfate and concentrated to an oil. The crude product was used directly in the next step without purification.

To a stirred solution of the above crude product in methanol (30 mL) was added a solution of aqueous sodium hydroxide (25 mL, 3 N) at room temperature. After 18 hours, water (20 mL) was added followed by aqueous hydrochloric acid (5N) to adjust the pH of solution to 10, then the solution was extracted with diethyl ether (2×25 mL). The organic layers were discarded. The aqueous layer was further acidified to the Congo red indicator endpoint and extracted with ethyl acetate (3×100 mL). The combined extracts were dried over sodium sulfate and concentrated to an oil (6.90 g).

A suspension of the above product and 5% palladium on activated carbon (0.37 g) in ethyl acetate (80 mL) was shaken under 30 psi of hydrogen at room temperature. After 17 hours the catalyst was removed and washed with ethyl acetate. The filtrate was concentrated to an oil. Flash chromatography (silica gel, 25% methanol in dichloromethane) gave the desired product (4.36 g, overall yield 64.8%) as an oil: IR (neat film) cm$^{-1}$ 3550-2550 (broad), 2974, 2936, 2879, 1750, 1704, 1399, 1367, 1162, 1097, 1010, 907, 856, 771; $^1$H NMR (300 MHz, CDCl$_3$) ppm 0.91 (t, 3H, J=7.2 Hz), 1.43 & 1.48 (2 x s, 9H), 1.57 (q, 2H, J=7.2 Hz), 2.24 (m, 2H), 3.37 (m, 2H), 4.05 (m, 1H), 9.92 (s, 1H);

EXAMPLE 8

This Example demonstrates the preparation of N-Boc-D-trans-4-methoxyproline.

To a stirred solution of N-Boc-D-cis-4-hydroxyproline methyl ester (9.14 g, 37.3 mmol), pyridine (13.9 mL, 170 mmol), and 4-dimethylaminopyridine (0.228 g, 1.87 mmol) in methylene chloride (50 mL) at 0° C. was added p-toluenesulfonyl chloride (15.6 g, 82.1 mmol) in portions. The mixture was stirred at 0° C. for 1 hour then allowed to warm to room temperature (22° C.) and kept for 2 days. Ice water (100 mL) was added and the mixture stirred 10 min. The organic layer was separated and washed with aqueous hydrochloric acid (60 mL, 0.34N), with saturated sodium bicarbonate solution (60 mL), with water (50 mL), and with brine (60 mL). Drying (sodium sulfate) and flash chromatography (silica gel, gradient of ethyl acetate:hexane 4:6 to 1:0) gave N-Boc-D-cis-4-(p-toluene-sulfonyloxy)proline methyl ester as a white solid (12.3 g, 82.3%): mp 70–72° C.

To a stirred solution of N-Boc-D-cis-4-(p-toluene-sulfonyloxy)proline methyl ester (5.88 g, 14.7 mmol) in toluene (60 mL) was added tetrabutylammonium acetate (5.77 g, 19.1 mmol) and the resultant solution was refluxed for 2.5 hours. The reaction mixture was washed with water (2×30 mL) and dried over sodium sulfate. Flash chromatography (silica gel, gradient of ethyl acetate:hexane 1:3 to 1:0) gave N-Boc-D-trans-4-acetoxyproline methyl ester (3.70 g, 87.6%) as an oil.

To a stirred solution of N-Boc-D-trans-4-acetoxyproline methyl ester (3.70 g, 12.9 mmol) in methanol (20 mL) at 0° C. was added a solution of potassium hydroxide (3.88 g, 69.1 mmol) in water (20 mL). After 4 hours at room temperature (22° C.), water (40 mL) was added and the mixture was extracted with diethyl ether (2×13 mL). The combined organics were discarded and the aqueous layer was acidified with aqueous hydrochloric acid (5 N) to the Congo red indicator endpoint. The mixture was extracted with ethyl acetate (3×100 mL) and the combined extracts were dried over sodium sulfate. Concentration gave N-Boc-D-trans-4-hydroxyproline (2.36 g, 78.9%) as a foam.

To a stirred suspension of hexane washed sodium hydride (0.77 g, 80%, 26 mmol) in anhydrous dimethylformamide (30 mL) was added a solution of N-Boc-D-trans-4-hydroxyproline (2.30 g, 9.90 mmol) at room temperature under argon. After 30 min, the suspension was treated with iodomethane (3.51 g, 24.8 mmol) at room temperature. After 26 hours, water (35 mL) followed by aqueous hydrochloric acid (5 N) was added to the reaction mixture until the Congo red indicator endpoint was reached. The aqueous solution was extracted with diethyl ether (3×65 mL) and the combined extracts were dried over sodium sulfate. Concentration gave an oil. The crude product was used directly in the next step without purification.

To a stirred solution of above crude product in methanol (10 mL) was added a solution of aqueous sodium hydroxide (9 mL, 3.0 N) at room temperature. After 5 hours, water (15 mL) was added and the mixture was extracted with diethyl ether (2×12 mL). The organics were discarded. The aqueous layer was acidified to the Congo red indicator endpoint and extracted with ethyl acetate (3×50 mL). The combined extracts were dried over sodium sulfate. Concentration followed by flash chromatography (silica gel, 20% methanol in methylene chloride) gave the desired product (1.65 g, 68.0%) as a glass: IR (neat film) cm$^{-1}$ 3500-2500 (broad), 2980, 2933, 1748, 1699, 1403, 1367, 1254, 1164, 1126, 1097, 989, 910, 853, 771; $^1$H NMR (300 MHz, CDCl$_3$) ppm 1.42 & 1.48 (2 x s, 9H), 2.22 (m, 2H), 3.32 (s, 3H), 3.58 (m, 2H), 3.98 (m, 1H), 4.30 (m, 1 H), 9.34 (s, 1H);

EXAMPLE 9

This Example demonstrates the preparation of N-Boc-L-cis-4-(cyclohexylmethoxy)proline.

To a stirred suspension of sodium hydride (0.64 g, 80%, 22 mmol) in anhydrous tetrahydrofuran (40 mL) was added in small portions N-Boc-L-cis-4-hydroxyproline (2.0 g, 8.6 mmol) at room temperature under argon. After 1 hour, the suspension was treated with cyclohexylmethyl bromide (2.90 mL, 20.8 mmol) at room temperature. The reaction mixture was heated to reflux for 6 hours, then stirred overnight at room temperature. The reaction mixture was acidified with aqueous hydrochloric acid to the Congo red indicator endpoint and extracted with ethyl acetate (3×40 mL). The combined extracts were dried over sodium sulfate. Flash chromatography (silica gel, 2% acetic acid in ethyl acetate) gave the desired product (0.69 g, 24%) as a waxy solid: IR (KBr) cm$^{-1}$ 3300-2600, 1721, 1630, 1434, 1365, 1249, 1167, 1092, 897, 848, 761; $^1$H NMR (300 MHz, CDCl$_3$) ppm 0.90 (m, 2H), 1.20 (m, 4H), 1.46 (m, 9 H), 1.68 (m, 5H), 2.31 (s, 1H), 2.61 (m, 1H), 3.19 (m, 2H) 3.56 (m, 2H) 4.02 (m, 1 H), 4.36 (m, 1H).

EXAMPLE 10

This Example demonstrates the preparation of N-Boc-D-trans-4-(3-methylbutoxy)proline.

To a stirred suspension of sodium hydride (1.24 g, 80%, 41.5 mmol) [washed with anhydrous hexane (2×20 mL) in anhydrous tetrahydrofuran (72 mL) was added a solution of N-Boc-D-trans-4-hydroxyproline (0.5 g/mL, 8.0 mL, 17 mmol) in anhydrous tetrahydrofuran at room temperature under argon. After 40 min, the mixture was treated with 4-bromo-2-methyl-2-butene (6.34 g, 42.5 mmol) and was heated to reflux for 4 hours. The mixture was cooled to room temperature and stirred overnight. The reaction mixture was diluted with water and extracted with ethyl acetate (3×160 mL). The combined organic layers were dried over sodium sulfate and concentrated to an oil which was used directly in the next step without purification.

To a stirred solution of the above crude product in methanol (25 mL) was added aqueous sodium hydroxide (8 mL, 3N, 24 mmol) at room temperature. The mixture was stirred for 5 hours. Water was added and the mixture was extracted with diethyl ether (3×20 mL). The combined organic layers were discarded and the aqueous layer was acidified with aqueous hydrochloric acid (5N) to the Congo red indicator endpoint. The mixture was extracted with ethyl acetate (3×120 mL), the combined extracts were dried over sodium sulfate, and concentrated to a yellow oil.

A suspension of the above product and 5% platinum on activated carbon (0.51 g) in ethyl acetate (45 mL) was shaken under 32 psi of hydrogen at room temperature. After 6 hours, the catalyst was removed and washed with ethyl acetate. The combined filtrates were concentrated to an oil. Flash chromatography (silica gel, methanol/dichloromethane/acetic acid 10:90:1) gave the desired product (2.79 g, overall yield 53.7%) as an oil: IR (neat film) cm$^{-1}$ 3500-2600 (broad), 1750, 1702, 1401, 1368, 1164, 910, 858, 771; $^1$H NMR (300 MHz, CDCl$_3$) ppm 0.89 (d, 6H, J=6.6 Hz), 1.42 & 1.47 (2 x s, 9H), 1.45 (m, 2H, overlapped), 1.67 (m, 1H), 2.16 (m, 1H), 2.36 (m, 1H), 3.38 (m, 2H), 3.48 (m, 4H), 4.05 (m, 1H), 4.38 (m, 1H), 8.59 (s, 1H).

Dicyclohexylamine salt (recrystallized from heptane): mp 124–125° C.(dec); $[\alpha]^{24}_D$=+24.4 (c=1.01, methanol). Anal. Calcd for C$_{27}$H$_{50}$N$_2$O$_5$(482.71 g/mol): C, 67.18; H, 10.44; N, 5.80. Found: C, 67.11; H, 10.49; N, 5.77.

EXAMPLE 11

This Example demonstrates the preparation of N-Boc-D-trans-4-(3-phenylpropoxy)proline To a stirred suspension of sodium hydride (1.65 g, 80%, 55.0 mmol) [washed with anhydrous hexane (2×15 mL)] in anhydrous dimethylformamide (90 mL) was added a solution of N-Boc-D-trans-4-hydroxyproline (5.03 g, 21.8 mmol) in anhydrous dimethylformamide (25 mL) at room temperature under argon. After 40 min, the mixture was treated with a solution of cinnamyl bromide (10.21 g, 50.3 mmol) in dimethylformamide (20 mL) and was heated to 50° C. for 5 hours The mixture was cooled to room temperature and diluted with water, and acidified with aqueous hydrochloric acid (1N) at the Congo red indicator endpoint. The mixture was extracted with ethyl acetate (4, 150 mL) and the combined organics were washed with half-saturated brine (1×140 mL). Concentrated to an oil which was used directly in the next step without purification.

To a stirred solution of the above crude product in methanol was added aqueous sodium hydroxide (12.0 mL, 3N, 36.0 mmol) at room temperature. The mixture was stirred for 17 hours, then water was added and the mixture was extracted with diethyl ether (3×30 mL). The combined organic layers were discarded, the aqueous layer was acidified with aqueous hydrochloric acid (5N) to the Congo red indicator endpoint, and extracted with ethyl acetate (2×150 mL, 2×100 mL). The combined organic extracts were washed with half-saturated brine (120 mL), dried over sodium sulfate, and concentrated to a yellow oil.

A suspension of the above product (5.76 g, 16.6 mmol) and 5% palladium on activated carbon (0.33 g) in ethyl acetate (85 mL) was shaken under 50 psi of hydrogen at 15° C. After 4.1 hours, the catalyst was removed and washed with ethyl acetate. The combined filtrates were concentrated to an oil. Flash chromatography (silica gel, 15% methanol in dichloromethane) gave a white solid. The solid was dissolved in dichloromethane and acidified with aqueous hydrochloric acid (5N) to the Congo red indicator endpoint, the mixture was extracted with dichloromethane (2×100 mL). The extract was washed with half-saturated brine (25 mL) and dried over sodium sulfate. Concentration gave the desired product (4.40 g, 76% overall) as an oil: IR (neat film) cm$^{-1}$ 3500-2500 (broad), 3026, 1746, 1702, 1605, 1417, 1403, 1368, 1162, 1106, 748, 700; $^1$H NMR (300 MHz, CDCl$_3$) ppm 1.43 & 1.49 (2 x s, 9H), 1.88 (m, 2H), 2.32 (m, 2H), 2.66 (m, 2H), 3.49 (m, 4H), 4.02 (m, 1H), 4.42 (m, 1H), 7.18 (m, 3H), 7.28 (m, 2H);

Cyclohexylamine salt (recrystallized from acetonitrile): mp 138.5–140.1° C.; $[\alpha]^{24}_D$=+23.6 (c=0.975, methanol); Anal. Calcd for C$_{30}$H$_{40}$N$_2$O$_5$ (448.61 g/mol): C, 66.94; H, 8.99; H, 6.24. Found C, 66.83; H, 8.98; N, 6.31.

EXAMPLE 12

This Example demonstrates the preparation of N-Boc-D-trans-4-(p-chlorophenylthio)proline.

To a stirred suspension of hexane washed sodium hydride (0.52 g, 80%, 17 mmol) in anhydrous tetrahydrofuran (80 mL) was added a solution of 4-chlorothiophenol (2.54 g, 18.3 mmol) in anhydrous tetrahydrofuran (20 mL) dropwise at room temperature under argon. After 0.5 hours, the clear mixture was treated with N-Boc-D-cis-4-(p-toluenesulfonyloxy)proline methyl ester (6.00 g, 15.0 mmol) at room temperature. The resultant white suspension was heated to reflux for 2.5 hours. After cooling to room temperature, the mixture was acidified to the Congo red indicator endpoint with aqueous hydrochloric acid (5N). The solution was extracted with ethyl acetate (3×120 mL) and the combined extracts dried over sodium sulfate. Concentration gave an oil which was used directly in the next step without purification.

To a stirred solution of the crude N-Boc-D-trans-4-(p-chlorophenylthio)proline methyl ester in methanol (20 mL) at room temperature was added aqueous sodium hydroxide (12.0 mL, 3N, 36.0 mmol). After 17 hours at room temperature, water was added and the mixture was extracted with diethyl ether (3×25 mL). The combined organics were discarded and the aqueous layer was acidified with aqueous hydrochloric acid (5N) to the Congo red indicator endpoint. The aqueous layer was extracted with ethyl acetate (3×150 mL) and the combined extracts dried over sodium sulfate. Flash chromatography (silica gel, 15% dichloromethane in methanol) gave a white solid. The solid was dissolved in ethyl acetate, washed with dilute aqueous hydrochloric acid, dried, and concentrated to give the desired product (4.07 g, 76%) as a foam: IR (neat film) cm$^{-1}$ 3300-2600, 2980, 1746, 1700, 1573, 1476, 1417, 1393, 1368, 1160, 1093, 1013, 905, 823, 771; $^1$H NMR (300 MHz, CDCl$_3$) ppm 1.41 & 1.47 (2 x s, 9H), 2.35 (m, 2H), 3.40 (m, 1H), 3.81 (m, 2H), 4.40 (m, 1 H), 7.51 (m, 4H), 8.87 (s, 1H).

Cyclohexylamine salt (recrystallized from acetonitrile): mp 174.5–176.2° C.; $[\alpha]^{23}_D$=+15.3 (c=0.98, methanol). Anal. Calcd for C$_{22}$H$_{33}$N$_2$O$_4$SCl (457.03 g/mol): C, 57.82; H, 7.28; N, 6.13. Found C, 57.77; H, 7.31; N, 6.18.

EXAMPLE 13

This Example demonstrates the preparation of N-Boc-D-trans-4-(2-naphthalenethio)proline.

To a stirred suspension of hexane washed sodium hydride (0.48 g, 80%, 16 mmol) in anhydrous tetrahydrofuran (80 mL) was added 2-naphthalenethiol (2.89 g 18.0 mmol) at room temperature under argon. After 1 hour, the mixture was treated with N-Boc-D-cis-4-(p-toluenesulfonyloxy)proline methyl ester (6.00 g, 15.0 mmol) at room temperature. The resultant mixture was heated to reflux for 4 hours. After cooling to room temperature, the mixture was stirred overnight. The mixture was diluted with water and acidified to the Congo red indicator endpoint with aqueous hydrochloric acid. The solution was extracted with ethyl acetate (3×100 mL) and the combined extracts dried over sodium sulfate. Concentration gave an off-white solid which was used directly in the next step without purification.

To a stirred solution of the crude N-Boc-D-trans-4-(2-naphthalenethio)proline methyl ester in methanol (40 mL) at room temperature was added a solution of aqueous sodium hydroxide (12.0 mL, 3N, 36.0 mmol). After 18 hours at room temperature, water was added and the mixture was extracted with diethyl ether (3×30 mL). The combined organics were discarded and the aqueous layer was acidified with aqueous hydrochloric acid (5N) to the Congo red indicator endpoint. The aqueous layer was extracted with ethyl acetate (4×120 mL) and the combined extracts dried over sodium sulfate. Concentration followed by flash chromatography (silica gel, dichloromethane/methanol 85:15) gave the desired product (3.92 g, 70.0% overall) as foam: IR (KBr) cm$^{-1}$ 3300-2500, 3050, 2978, 1746, 1700, 1589, 1416, 1368, 1160, 1131, 900, 853, 815, 746; $^1$H NMR (300 MHz, CDCl$_3$)ppm 1.39 & 1.44 (2 x s, 9H), 2.36 (m, 2H), 3.47 (m, 1H), 3.89 (m, 1H), 4.44 (m, 1 H), 7.45 (m, 3H), 7.75 (m, 3H), 7.86 (s, 1H), 10.50 (s, 1H).

Cyclohexylamine salt (recrystallized from acetonitrile): mp 186.5° C.–189.5° C. (dec); $[\alpha]^{23.5}_D$=+3.50° (c=1.00, methanol). Anal. Calcd for C$_{26}$H$_{36}$N$_2$O$_4$S (472.64 g/mol): C, 66.07; H, 7.68; N, 5.93. Found C, 65.84; H, 7.73; N, 5.87.

EXAMPLE 14

This Example demonstrates the preparation of N-Boc-D-cis-4-hydroxyproline methyl ester.

Thionyl chloride (34.0 mL, 461 mmol) was added dropwise with stirring to a flask containing methanol (650 mL) at 5° C. To this solution was added D-cis-4-hydroxyproline (50.10 g, 382.1 mmol) and the resulting mixture was heated to reflux. After 4.5 hours, the solution was cooled to room temperature and stirred for 19 hours. The mixture was filtered to remove a small amount of insoluble material then was concentrated to give a gel. This was triturated with boiling ethyl acetate to give, after cooling, amorphous white solids which were collected and dried in vacuo to afford crude D-cis-4-hydroxyproline methyl ester hydrochloride (70.13 g, 101%) as a white powder.

To a mechanically stirred solution of the crude ester hydrochloride and potassium carbonate (38.1 g, 276 mmol) in water (300 mL) and tetrahydrofuran (400 mL) was added a solution of di-t-butyl dicarbonate (100.0 mL, 422.2 mmol) in tetrahydrofuran (50 mL) dropwise at room temperature. After 22 hours, the mixture was diluted with diethyl ether (250 mL) and the layers separated. The aqueous layer was extracted with diethyl ether (3×200 mL) and the combined organics were washed with water (50 mL), with aqueous hydrochloric acid (50 mL, 0.25 N), and with brine (50 mL). The organics were dried (magnesium sulfate) and concentrated to a syrup which was dried in vacuo to give white solids. Trituration with boiling heptane followed by standing at room temperature gave N-Boc-D-cis-4-hydroxyproline methyl ester (75.83 g, 81% overall) as white crystals: mp 80–82° C.; IR (KBr) cm$^{-1}$ 3466, 2985, 1728, 1679, 1424, 1283, 1262, 1177, 1162, 1123, 1090; $^1$H NMR (300 MHz, CDCl$_3$) ppm 1.42 & 1.47 (2 x s, 9H), 2.05 (m, 1H), 2.32 (m, 1H), 3.59 (m, 3H), 3.78 & 3.79 (2 x s, 3H), 4.35 (m, 2H); $[\alpha]^{23}_D$=+64.8 (c=2.10, methanol). Anal. Calcd for C$_{11}$H$_{19}$NO$_5$ (245.28 g/mol): C, 53.87; H, 7.81; N, 5.71. Found: C, 53.91; H, 7.84; N, 5.70.

EXAMPLE 15

This Example demonstrates the preparation of N-Boc-D-cis-4-(n-propoxy)proline

To a stirred solution of D-cis-4-hydroxyproline (15.11 g, 116.1 mmol), sodium carbonate (24.50 g, 231.2 mmol), and 2-propanol (80 mL) in water (270 mL) at room temperature was added di-t-butyl dicarbonate (33.0 mL, 139 mmol). After 18 hours, the suspension was diluted with water (100 mL) and extracted with diethyl ether (3×200 mL). The diethyl ether extracts were discarded and the aqueous layer acidified to the Congo red indicator endpoint with concentrated hydrochloric acid with cooling (5° C.). The mixture was extracted with ethyl acetate (5×250 mL) and the combined organics dried (sodium sulfate). Concentration gave white solids which were recrystallized from acetonitrile to afford N-Boc-D-cis-4-hydroxyproline (21.04 g, 78%) as white crystals: mp 146–148° C. (dec);$[\alpha]_D$=+51.05 (c=2.18, MeOH).

To a stirred suspension of hexane washed sodium hydride (1.81 g, 60.3 mmol) in N,N-dimethylformamide (50 mL) under argon was added N-Boc-D-cis-4-hydroxyproline (5.55 g, 24.0 mmol) at room temperature (in portions to minimize foaming). After 30 min, the reaction mixture was treated with allyl bromide (5.30 mL, 60.6 mmol). The resulting yellow solution was stirred at room temperature for 26 hours, then diluted with aqueous hydrochloric acid (120 ml, 0.17 N) and diethyl ether (200 mL). The layers were separated and the aqueous layer extracted with diethyl ether (3×200 mL). The combined organics were washed with saturated aqueous sodium bicarbonate (50 mL) and dried (magnesium sulfate). Concentration gave crude N-Boc-D-cis-4-allyloxyproline allyl ester as an oil.

To a stirred solution of this oil in methanol (25 mL) was added aqueous sodium hydroxide (30 mL, 1.0 N) at room temperature. After 18 hours, the solution was diluted with water (30 mL) and extracted with diethyl ether (3×30 mL). The organics were discarded and the aqueous layer acidified to the Congo red indicator endpoint with concentrated hydrochloric acid, saturated with sodium chloride, and extracted with ethyl acetate (4×50 mL). The combined organics were dried (sodium sulfate) and concentrated to give crude N-Boc-D-cis-4-allyloxyproline as an oil.

A mixture of the oil and platinum on activated carbon (0.47 g) in ethyl acetate (60 mL) was shaken at room temperature under 40 psi of hydrogen for 6 hours. The solid was removed and washed with ethyl acetate. The combined filtrates were concentrated to an oil which was purified by flash chromatography (silica gel, 95:5:1 dichloromethane; methanol:acetic acid). Extensive drying in vacuo afforded N-Boc-D-cis-4-(n-propoxy)proline was waxy solids (4.90 g, 75%): mp 49–52° C.; IR (KBr) cm$^{-1}$ 3419, 2972, 1756, 1702, 1655, 1427, 1365, 1198, 1172, 1100, 1013, 887; $^1$H NMR (300 MHz, CDCl$_3$) ppm 0.85 (t, 3H, J=7.4 Hz), 1.43 (br m, 12H), 2.27 (m, 2H), 3.43 (br m, 3H), 3.99 (br s, 1H), 4.29 (m, 1H), 10.59 (br s, 1H); $[\alpha]_D$=+29.5 (c=2.03, MeOH).

Dicyclohexylammonium salt (recrystallized from acetonitrile): mp 164–166° C.; $[\alpha]^{23}_D$=+32.8 (c=1.03, methanol). Anal. Calcd for C$_{25}$H$_{46}$N$_2$O$_5$ (454.65 g/mol): C, 66.05; H, 10.20; N, 6.16. Found: C. 66.02; H, 10.18; N, 6.18.

EXAMPLE 16

This Example demonstrates the preparation of N-Boc-D-cis-4-ethoxyproline.

To a stirred suspension of sodium hydride (1.64 g, 80%, 54.5 mmol) [washed with anhydrous hexane, 2×20 mL] in anhydrous dimethylformamide (110 mL) was added in small portions N-Boc-D-cis-4-hydroxyproline (6.01 g, 25.9 mmol) at room temperature under argon. After 30 min, the suspension was treated with iodoethane (8.50 g, 54.5 mmol) at room temperature. After 24 hours, the reaction mixture was acidified with aqueous hydrochloric acid to the Congo red indicator endpoint and extracted with diethyl ether (3×170 mL). The combined extracts were dried over sodium sulfate and concentrated to an oil which was used directly in the next step without purification.

To a stirred solution of the crude product in methanol (15 mL) was added aqueous sodium hydroxide (15 mL, 3N, 45 mmol) at room temperature. After stirring overnight, water was added and the mixture was extracted with diethyl ether (3×20 mL). The organic extracts were discarded. The aqueous layer was acidified to the Congo red indicator endpoint and aqueous hydrochloric acid (5N) and extracted with ethyl acetate (3×150 mL). The combined extracts were washed with half-saturated brine (2×50 mL) and dried over sodium sulfate. Flash chromatography (silica gel, dichloromethane:methanol:acetic acid 90:8:2) gave the product (4.59 g, 68.4%) as a solid: mp. 51–53.5° C.; IR (KBr) cm$^{-1}$ 3500-2500, 1722, 1622, 1434, 1250, 1095, 897; $^1$H NMR (300 MHz, CDCl$_3$) ppm 1.17 (t, 3 H, J=6.9 Hz), 1.44 & 1.47 (2 x s, 9 H), 2.31 (m, 1H), 2.55 (m, 1H), 3.50 (m, 4H), 4.05 (m, 1 H), 4.39 (m, 1H), 10.47 (br s, 1H)

Dicyclohexylamine salt (recrystallized from heptane):mp 162.5–164° C.; $[\alpha]^{23}_D$=+34.1 (c=1.04, methanol). Anal. Calcd for C$_{24}$H$_{44}$N$_2$O$_5$ (426.60 g/mol): C, 65.42; H, 10.07; N, 6.36. Found: C, 65.34; H, 10.08; N, 6.34.

EXAMPLE 17

This Example demonstrates the preparation of N-Boc-L-cis-4-phenylthioproline.

To a stirred suspension of hexane washed sodium hydride (1.61 g, 80%, 53.6 mmol) in anhydrous tetrahydrofuran (120 mL) was added thiophenol (6.30 mL, 61.3 mmol) dropwise at room temperature under argon. After 1 hour, the mixture was treated with N-Boc-L-trans-4-(p-toluenesulfonyloxy) proline methyl ester (5.00 g, 12.5 mmol) at room temperature. The resultant mixture was heated to reflux for 7.5 hours, then cooled to room temperature and stirred overnight. The mixture was acidified to the Congo red indicator endpoint with aqueous hydrochloric acid and the layers were separated. The aqueous layer was extracted with ethyl acetate (3×100 mL) and the combined organics were dried over sodium sulfate. Concentration gave an oil which was used directly in the next step without purification.

To a stirred solution of the crude N-Boc-L-cis-4-phenylthioproline methyl ester in methanol (25 mL) at 5° C. was added aqueous sodium hydroxide (15 mL, 3 N, 45 mmol). The mixture was allowed to gradually warm to room temperature. After 18 hours at room temperature, water was added and the mixture was extracted with hexane (2×25 mL). The combined organics were discarded and the aqueous layer was acidified with aqueous hydrochloric acid (5 N) to the Congo red indicator endpoint. The aqueous layer was extracted with ethyl acetate (3×120 mL) and the combined extracts dried over sodium sulfate. Concentration followed by flash chromatography (silica gel, dichloromethane/methanol/acetic acid 90:10:1) gave the desired product (5.60 g, 98.8%) as a white, hygroscopic solid: mp 76–79.5° C.; IR (neat film) cm$^{-1}$ 3500-2500, 1699 (br), 1584 (w), 1478, 1416, 1159, 743, 691; $^1$H NMR (300 MHz, CDCl$_3$) ppm 1.42 & 1.47 (2 x s, 9H), 2.22 (m, 1H), 2.65 (m, 1H), 3.38 (m, 1H), 3.66 (m, H), 3.92 (m, 1 H), 4.34 (m, 1 H), 7.29 (m, 3H), 7.42 (d, 2H, J=6.6 Hz), 9.45 (s, 1H).

Dicyclohexylamine salt (recrystallized from acetonitrile): mp 168–169.2° C.; $[\alpha]^{23}_D$=−44.2 (c=1.03, methanol). Anal. Calcd for C$_{28}$H$_{44}$N$_2$O$_4$S (504.73 g/mol): c, 66.63; H, 8.79; N, 5.55. Found: C, 66.56; H, 8.82; N, 5.53.

EXAMPLE 18

This Example demonstrates the preparation of N-Boc-D-cis-4-phenylthioproline.

To a stirred solution of N-Boc-D-cis-4-hydroxyproline methyl ester (2.51 g, 10.2 mmol) and carbon tetrabromide (1.28 g, 30.7 mmol) in anhydrous dichloromethane (20 mL) at 5 ° C. was added triphenylphosphine (8.42 g, 31.8 mmol) under argon. The resulting mixture was warmed to room temperature. After 22 h at room temperature, the suspension was diluted with methanol (5 mL) and stirred for 1.5 hours. The suspension was diluted with diethyl ether (30 mL), filtered, and the solids washed with diethyl ether (3×20 mL). The combined filtrates were concentrated to an oil which was purified by flash chromatography (silica gel, 25% ethyl acetate in hexanes) to afford N-Boc-D-trans-4-bromoproline methyl ester (2.62 g, 83%) as a colorless oil.

To a stirred suspension of pentane washed sodium hydride (0.32 g, 80%, 10 mmol) in anhydrous tetrahydrofuran (40 mL) was added thiophenol (1.12 mL, 10.6 mmol) at room temperature. After gas evolution had ceased, the suspension was treated with a solution of N-Boc-D-trans-4-bromoproline methyl ester (2.50 g, 8.11 mmol) in anhydrous tetrahydrofuran (5 mL). The suspension was heated to reflux for 3 hours, cooled to room temperature, diluted with water (20 mL), and acidified to the Congo red indicator endpoint with aqueous hydrochloric acid (5 N). The solution was extracted with diethyl ether (4×50 mL), the combined organics were washed with brine, and dried over sodium sulfate. Concentration gave crude N-Boc-D-cis-4-(phenylthio) proline methyl ester as an oil.

To a solution of this oil in methanol (20 mL) was added aqueous sodium hydroxide (5.5 mL, 3.0 N, 16.5 mmol) and the mixture was stirred at room temperature for 5 hours. The mixture was diluted with water (20 mL) and concentrated to remove most of the methanol. The aqueous solution was extracted with diethyl ether (3×10 mL) and the combined organics discarded. The aqueous layer was cooled to 5° C., acidified to the Congo red indicator endpoint with aqueous hydrochloric acid (5 N), and extracted with ethyl acetate (4×20 mL). The combined organics were dried (sodium sulfate) and concentrated to an oil which was purified by flash chromatography (silica gel, 1% acetic acid and 6% methanol in chloroform) to afford the desired product (2.18 g, 83% as a colorless glass: IR (neat film) cm$^{-1}$ 3600-2600, 1700 (broad), 1478, 1419, 1399, 1368, 1254, 1159, 1123, 912, 739, 691; $^1$H NMR (300 MHz, CDCl$_3$) ppm 1.41 & 1.47 (2 x s, 9H), 2.10 (m, 0.5H), 2.27 (m, 0.5H), 2.65 (m, 1H), 3.38 (m, 1H), 3.65 (m, 1H), 3.94 (m, 1H), 4.35 (m, 1H), 7.29 (m, 2H), 7.42 (m, 3H), 9.09 (br s, 1H).

Dicyclohexylamine salt (recrystallized from acetonitrile): mp 167–168° C.;$[\alpha]^{22}_D$=+44.0 (c=1.04, methanol). Anal. Calcd for C$_{28}$H$_{44}$N$_2$O$_4$S (504.73 g/mol): C, 66.63; H, 8.79; N, 5.55. Found: C, 66.45; H, 8.82; N, 5.60.

EXAMPLE 19

This Example demonstrates the preparation of N-Boc-L-cis-4-phenoxyproline.

To a stirred solution of t-butyl nitrite (0.87 g, 7.45 mmol) in DMF (3 mL) at 60° C. was added dropwise a solution of N-Boc-L-cis-4-(4-aminophenoxy)proline methyl ester (1.67 g, 4.96 mmol) over 10 minutes. The mixture was stirred at 60° C. for 10 minutes, then allowed to cool to room temperature (22° C.). Ether (30 mL) was added. The solution was then poured into aqueous hydrochloric acid (20% HCl). The organic layer was separated and washed with aqueous saturated sodium bicarbonate solution. Drying (MgSO$_4$), flash chromatography (silica gel, gradient of hexane:ethyl acetate 90:10 to 85:15) yielded N-Boc-L-cis-4-phenoxyproline methyl ester (0.51 g, 32%) as a crystalline solid.

To a solution of N-Boc-L-cis-4-phenoxyproline methyl ester (0.51 g, 1.59 mmol) in DME (8.5 mL) at 0° C. was added lithium hydroxide monohydrate (0.077 g, 1.80 mmol). The suspension was stirred overnight. After the addition of ethyl acetate (10 mL) and water (25 mL), the solution was quenched with aqueous hydrochloric acid (5 ML, 1N). The organic layer was separated and washed with brine, dried over sodium sulfate, filtered, and evaporated to yield with product (0.47 g, 92%): mp 133–135° C. IR (KBr) cm$^{-1}$ 3438, 3055, 2975, 2934, 2816, 2623, 1723, 1630, 1599, 1489, 1435, 1368, 1293, 1250, 1229, 1165, 1183, 897, 756, 692; $^1$H NMR (300 MHz, CDCl$_3$) ppm 1.46 (s, 9H), 2.42 (bs, 1H), 2.53 (bs, 1H), 2.73 (bs, 1H), 3.73 (bs, 2H), 4.51 (bs, 1H), 4.92 (m, 1H), 6.83 (t, 1H, J=7.9Hz) 6.96 (t, 1H, J=7.3 Hz), 7.26 (t, 1H, J=7.69 Hz), 9.09 (br s, 1H).

EXAMPLE 20

This Example demonstrates the preparation of N-Boc-(2S, 3aS, 7aS)-Octahydro-1H-indole-2-carboxylic Acid (Oic).

A mixture of (S)-indoline-2-carboxylic acid (10.01 g, 60.73 mmol) and 10% platinum on activated carbon (0.57 g) in aqueous hydrochloric acid (150 mL, 1 N, 150 mmol) and ethanol (20 mL) was shaken in a Parr bottle under 45 psi of hydrogen at room temperature (22° C.). After 20 hours, the mixture was filtered and the solids washed with methanol. The combined filtrates were concentrated to 50 mL and the solution treated with sodium carbonate (9.65 g, 91 mmol) di-tert-butyl dicarbonate (17.5 mL, 77.4 mmol) and 20 mL of dioxane. The mixture was stirred for 18 hours, diluted with water (50 mL), and the mixture extracted with ethyl ether (3×30 mL). The aqueous layer was decolorized with charcoal, acidified to the Congo red indicator endpoint with concentrated hydrochloric acid, saturated with sodium chloride and extracted with ethyl acetate (5×50 mL). The combined extracts were dried (sodium sulfate) and the solvent removed to give a white foam. Recrystallization from heptane gave the carboxylic acid (11.51 g, 70%) as white crystals: mp 129–131° C.

EXAMPLE 21

This Example demonstrates the preparation of N-Boc-D-trans-4-(p-methylphenylthio)proline.

To a stirred suspension of hexane washed sodium hydride (0.53 g, 80%, 18 mmol) in anhydrous tetrahydrofuran (100 mL) was added p-thiocresol (2.31 g, 18.6 mmol) at room temperature under argon. After 45 minutes, the suspension was treated with N-Boc-D-cis-4-(p-toluenesulfonyloxy) proline methyl ester (6.00 g, 15.0 mmol) at room temperature. The resultant mixture was stirred at room temperature for 23 hours. The mixture was added with water and acidified to the Congo red indicator endpoint with aqueous hydrochloric acid (5N). The solution was extracted with ethyl acetate (3×160 mL) and the combined extracts dried over sodium sulfate. Concentration gave an oil which was used directly in the next step without purification.

To a stirred solution of the crude N-Boc-D-trans-4-(p-methylphenylthio)proline methyl ester in methanol (20 mL) at room temperature was added aqueous sodium hydroxide (12.0 mL, 3N, 36.0 mmol). After 17 hours at room temperature, water was added and the mixture was extracted with diethyl ether (3×20 mL). The combined organics were discarded and the aqueous layer was acidified with aqueous hydrochloric acid (5 N) to the Congo red indicator endpoint. The aqueous layer was extracted with ethyl acetate (3×150 mL) and the combined extracts dried over sodium sulfate. Flash chromatography (silica gel, 15% dichloromethane in methanol) gave a white solid. The solid was dissolved in ethyl acetate, washed with dilute aqueous hydrochloric acid, dried, and concentrated to give the desired product (4.10 g, 81%) as a foam: IR (neat film) cm$^{-1}$ 3300-2500, 2975, 1746, 1702, 1478, 1419, 1397, 1368, 1160, 1131, 900, 810, 771: $^1$H NMR (300 MHz, CDCl$_3$) ppm 1.40 & 1.48 (2 x s, 9H), 2.19 (m, 1H), 2.34 (s, 3H), 2.51 (m, 1H), 3.41 (m, 1H), 3.77 (m, 2H), 4.41 (m, 1 H), 7.14 (d, 2H, J=7.5 Hz), 7.33 (d, 2H, J=7.5 Hz), 8.71 (s, 1H); [α]$^{23.5}_D$=+26.5 (c=2.00, methanol).

Cyclohexylamine salt (recrystallized from acetonitrile): mp 180–182° C.; [α]$^{23}_D$=+19.8 (c=1.02, methanol). Anal. Calcd for C$_{23}$H$_{36}$N$_2$O$_4$S (436.61 g/mol): C, 63.27; H, 8.31; N, 6.42. Found: C, 63.18; H, 8.36; N, 6.45.

EXAMPLE 22

This Example demonstrates the preparation of N-Boc-D-trans-4-ethoxyproline.

The stirred suspension of sodium hydride (1.30 g, 80%, 43.3 mmol) [washed with hexane (2×15 mL) in anhydrous tetrahydrofuran (75 mL) was added a solution of N-Boc-D-trans-4-hydroxyproline in tetrahydrofuran (0.5 g/mL, 8.0 mL, 17 mmol) slowly at room temperature and under argon. After 40 minutes, the suspension was treated with iodoethane (3.50 mL, 43.8 mmol) at room temperature. The reaction mixture was heated to reflux for 3.5 hours, then cooled to room temperature. The reaction mixture was diluted with water and tetrahydrofuran was removed under reduced pressure. The aqueous solution was extracted with diethyl ether (3×30 mL). The combined extracts were discarded. The aqueous layer was acidified with aqueous hydrochloric acid (5N) to the Congo red indicator endpoint and extracted with ethyl acetate (4×100 mL). The combined extracts were dried over sodium sulfate. Flash chromatography (silica gel, 20% methanol in dichloromethane) gave the desired product (2.91 g, 65%) as a wax: IR (KBr) cm$^{-1}$ 3500-2600, 1738, 1640, 1434, 1367, 1316, 1247, 1172, 1134, 1100, 917, 771; $^1$H NMR (300 MHz, CDCl$_3$) ppm 1.19 (t, 3 H, J=6.9 Hz), 1.42 & 1.48 (2 x s, 9 H), 2.17 (m, 1H), 2.38 (m, 1H), 3.50 (m, 4H), 4.08 (m, 1H), 4.38 (m, 1H), 8.71 (2, 1H).

Dicyclohexylamine salt (recrystallized from heptane): mp 129.5–131° C.; [α]$^{24}_D$=+28.6 (c=0.99, methanol). Anal. Calcd for C$_{24}$H$_{44}$N$_2$O$_4$ (440.62 g/mol): C, 65.42; H, 10.07; N, 6.36. Found: C, 65.33; H, 10.08; N, 6.38.

EXAMPLE 23

This Example demonstrates the preparation of N-Boc-L-cis-4-ethoxyproline.

To a stirred suspension of sodium hydride (1.94 g, 80%, 64.8 mmol) in anhydrous dimethylformamide (100 mL) was added in small portions N-Boc-L-cis-4-hydroxyproline (6.0 g, 26 mmol) at room temperature under argon. After 30 minutes, the suspension was treated with iodoethane (5.20 mL, 54.5 mmol) at room temperature. After 27 hours, the reaction mixture was acidified with aqueous hydrochloric acid solution to the Congo red indicator endpoint and extracted with diethyl ether (3×100 mL). The combined extracts were washed with half-saturated brine, dried over sodium sulfate, and concentrated to an oil which was used directly in the next step without purification.

To a stirred solution of the product in methanol (25 mL) was added aqueous sodium hydroxide solution (20 mL, 3N, 60 mmol) at room temperature. After stirring 6 hours, water was added and the mixture extracted with diethyl ether (2×20 mL). The organic extracts were discarded. The aqueous layer was acidified to the Congo red indicator endpoint and extracted with ethyl acetate (3×100 mL). The combined extracts were dried over sodium sulfate. Flash chromatography (silica gel, 15% methanol in dichloromethane) gave the desired product (5.50 g, 68.4%) as a solid: mp 53–56.2° C.; IR (KBr) cm$^{-1}$ 3500-2500, 1723, 1622, 1434, 1250, 1095, 897, 848, 769; $^1$H NMR (300 MHz, CDCl$_3$) ppm 1.18 (t, 3 H, J=6.6 Hz), 1.46 (s, 9 H), 2.32 (m, 2H), 3.51 (m, 4H), 4.06 (M, 1 H), 4.37 (m, 1H), 8.20 (s, 1H).

Dicyclohexylamine salt (recrystallized from heptane): mp 161–162.4° C.; $[\alpha]^{23.5}_D$=−33.5 (c=0.98, methanol). Anal. Calcd for C$_{24}$H$_{44}$N$_2$O$_5$ (440.62 g/mol): C, 65.42; H, 10.07; N, 6.36. Found: C, 65.32; H, 10.05; N, 6.37.

EXAMPLE 24

This Example demonstrates the preparation of N-Boc-L-trans-4-ethoxyproline.

To a stirred suspension of hexane washed sodium hydride (1.56 g, 80%, 51.9 mmol) in anhydrous tetrahydrofuran (100 mL) was added in small portions N-Boc-L-trans-4-hydroxyproline (6.00 g, 25.9 mmol) at room temperature and under argon. After 1 hour, the suspension was treated with iodoethane (4.15 mL. 51.9 mmol) at room temperature. The reaction mixture was heated to reflux for 3 hours, then cooled to room temperature and stirred overnight. The reaction mixture was diluted with water and extracted with hexane (30 mL). The hexane extract was discarded. The aqueous layer was acidified with concentrated hydrochloric acid to the Congo red indicator endpoint and extracted with ethyl acetate (3×120 mL). The combined extracts were dried over sodium sulfate. Flash chromatography (silica gel, methanol:dichloromethane:acetic acid 10:90:1) gave the desired product (4.98 g, 74.2%) as a solid: mp 48.5–51.2° C.; IR (KBr) cm$^{-1}$ 3500-2600, 1738, 1640, 1434, 1367, 1244, 1172, 1100, 771; $^1$H NMR (300 MHz, CDCl$_3$) ppm 1.20 (t, 3 H, J=6.9 Hz), 1.42 & 1.48 (2 x s, 9 H), 2.25 (m, 2H), 3.51 (m, 4H), 4.08 (m, 1 H), 4.35 (t, ½H, J=7.8 Hz), 4.44 (m, ½H), 9.06 (s, 1H).

Dicyclohexylamine salt (recrystallized from heptane): mp 128.5–130.5° C.; $[\alpha]^{21.5}_D$=−30.2 (c=1.02, methanol). Anal. Calcd for C$_{24}$H$_{44}$N$_2$O$_4$ (440.62 g/mol): C, 65.42; H, 10.07; N, 6.36. Found: C, 65.31; H, 10.02; N, 6.38.

EXAMPLE 25

This Example demonstrates the preparation of N-Boc-L-trans-4-phenylthioproline.

To a stirred suspension of hexane washed sodium hydride (1.35 g, 80%, 45.1 mmol) in anhydrous tetrahydrofuran (90 mL) was added thiophenol (3.90 mL, 38.0 mmol) dropwise at room temperature under argon. After 40 minutes, the mixture was treated with N-Boc-L-cis-4-(p-toluenesulfonyloxy)proline methyl ester (10.0 g, 25.0 mmol) at room temperature overnight. After 16 hours, the mixture was diluted with water and acidified to the Congo red indicator endpoint with aqueous hydrochloric acid (5N). The solution was extracted with ethyl acetate (3×100 mL) and the combined extracts dried over sodium sulfate. Concentration gave an oil which was used directly in the next step without purification.

To a stirred solution of the crude N-Boc-L-trans-4-phenylthioproline methyl ester in methanol (30 mL) at room temperature was added aqueous sodium hydroxide (18.0 mL, 3N, 54 mmol). After 18 hours, water was added and the mixture was extracted with diethyl ether (3×20 mL). The combined organics were discarded and the aqueous layer was acidified with aqueous hydrochloric acid (5N) to the Congo red indicator endpoint. The aqueous layer was extracted with ethyl acetate (4×120 mL) and the combined extracts dried over sodium sulfate. Concentration gave a yellow oil which was used in next step without purification.

The oil was dissolved in acetonitrile at room temperature and treated with cyclohexylamine (3.30 mL, 28.8 mmol). The precipitated solid was recrystallized in the same solvent. The crystalline product was dissolved in water and acidified with aqueous hydrochloric acid (5 N) to the Congo red indicator endpoint. The aqueous layer was extracted with ethyl acetate (3×120 mL) and the combined extracts dried over sodium sulfate. Concentration gave N-Boc-L-trans-4-phenylthioproline (6.85 g, 85%) as an foam: IR (film) cm$^{-1}$ 3300-2500, 1749, 1702, 1583, 1415, 1398, 1368, 1164, 743; $^1$H NMR (300 MHz, CDCl$_3$) ppm 1.45 & 1.48 (2 x s, 9H), 2.31 (m, 2H), 3.44 (m, 1H), 3.76 (m, 2H), 4.43 (m, 1H), 7.36 (m, 3H), 7.42 (m, 2H), 9.77 (s, 1H); $[\alpha]^{23.5}_D$=−26.9 (c 2.04, methanol).

Dicyclohexylamine salt (recrystallized from acetonitrile): mp 164.5–165.8° C.; $[\alpha]^{24.5}_D$=−16.0 (c 1.00, methanol). Anal. Calcd for C$_{28}$H$_{44}$N$_2$O$_4$S (504.73 g/mol): C, 66.63; H, 8.79; N, 5.55. Found: C, 66.65; H, 8.81; N, 5.57.

Cyclohexylamine salt (recrystallized from acetonitrile): mp 170–172.5° C.; $[\alpha]^{23.5}_D$=−18.5 (c 1.02, methanol). Anal. Calcd for C$_{22}$H$_{34}$N$_2$O$_4$S (422.58 g/mol): C, 62.53; H, 8.11; N, 6.63. Found: C, 62.52; H, 8.13; N, 6.62.

EXAMPLE 26

General Procedure for Automated Peptide Synthesis: Preparation of D-Arg-Arg-Pro-4Hyp-Gly-Thi-Ser-(D-4-hydroxyproline Cis Propyl Ether)-Tic-Arg The peptide was synthesized employing t-Boc chemistry on a solid phase synthesizer (Milligen Biosearch 9600 Peptide Synthesizer). Boc-Arg(Tos)-PAM resin (Applied Biosystems) (PAM=phenylacetamidomethyl), 0.25 g, with a resin substitution of 0.62 mmol Arg/gram of resin, was placed in the reaction vessel and subjected to Procedure A for the coupling of Boc-Oic. Commercially available amino acids were purchased from Bachem Bioscience. Volumes of reagents and solvents were approximately 20 ml/gram of resin.

Procedure A:

1. Deprotection: Removal of the t-butyloxycarbonyl-protecting group (Boc) was achieved by treatment of the resin with deblocking reagent (trifluoroacetic acid (TFA)/anisole/dichloromethane (DCM) 45:2.5:52.5 v/v containing 1 mg/mL of indole), two times for one minute and once for twenty minutes. The resin was then washed with DCM several times, followed by neutralization with base [10% diisopropylethylamine (DIEA) in DCM], three times for one minute. The resin was subsequently washed with DCM and dimethylformamide (DMF).

2. Coupling: All couplings and recouplings were mediated in the same manner. Boc-Oic (1.47 mol, 0.4 M in DMF) was mixed with one equivalent of diisopropylcarbodiimide (DIPCDI) (1.47 mmol, 0.4 M in DCM) for a two minute activation period prior to coupling with the resin. The mixture was added to the reaction vessel containing the resin and mixed for two hours. Coupling efficiency of the amino acid to the growing peptide chain on the resin was checked. Incomplete coupling of an amino acid resulted in a recoupling step. Recoupling involved washing the resin-peptide three times for one minute with base followed by DCM and DMF. Amino acid activation with DIPCDI with addition to the peptide-resin was repeated and allowed to mix an additional two hours. After a successful coupling the peptide-resin was washed several times with DCM.

3. Capping: The growing peptide chain was capped on the α-amino group by acetylation with 1-acetylimidazole (0.3 M in DMF) at the end of each coupling or recoupling. The resin was washed three times with base followed by DCM and DMF. The resin was treated with capping reagent for 30 minutes and then washed with DMF.

Procedure B:

The N-terminal protecting group was removed by the following procedure:

Terminal deprotection: Following the capping of the final amino acid to be added to the growing peptide chain, the peptide-resin was treated with deblocking reagent (TFA/anisole/DCM) twice for one minute and once for 20 minutes. The resin was washed with DCM followed by methanol and then dried by a stream of inert gas.

The following amino acids were added to the growing peptide chain according to the listed programs: Boc-D-Phe (A), Boc-Ser(Bzl) (A), Boc-Thi (A), Boc-Gly (A), Boc-4 Hyp(Bzl) (A), Boc-Pro (A), Boc-Arg(Tos) (A), Boc-D-Arg (Tos) (A),(B). This yielded 0.481 g of protected peptide-resin as the TFA salt.

HF Cleavage: The peptide-resin (0.481 g) was suspended in 5 mL of liquid anhydrous HF (ratio of 10 mL HF/g resin) containing 0.48 mL of anisole at −70° C. and stirred for 60 minutes at 0° C. The HF was removed by a stream of nitrogen gas followed by vacuum (water aspirator). The resin was washed three times with 30 mL of ethyl ether and dried under high vacuum for 30 minutes. The peptide was extracted with distilled deionized water (200 mL) and the solution was lyophilized to give 176 mg of crude deprotected peptide.

Purification: The peptide was purified on a reverse phase C-18 (2×25 cm) Vydac HPLC column using a gradient of 0.1% TFA/H2O and acetonitrile (0.1% TFA) to give 53 mg of purified deprotected peptide.

Analysis: Purified peptide was characterized by amino acid analysis and gave the following results: Arg, 2.9 (3.0); Ser, 0.92 (1.0); Thi, 1.09 (1.0); Gly, 1.0 (1.0).

The peptide was also characterized by mass spectrometry (JEOL HX110/110 FAB) [M+H] obsd 1308.7, [M+H] calcd 1308.6.

EXAMPLE 27

Preparation of D-Arg-Arg-Pro-4Hyp-Gly-Thi-Ser-(D-4-hydroxyproline cis methyl ether)-Tic-Arg Using the method of Example 26, the peptide D-Arg-Arg-Pro-4Hyp-Gly-Thi-Ser-(D-4-hydroxyproline cis methyl ether)-Tic-Arg was prepared. Purified peptide was characterized by amino acid analysis and gave the following results: Arg, 3.38 (3.0); Ser, 0.84 (1.0); Thi, 1.14 (1.0); Gly, 1.0 (1.0). The peptide was also characterized by mass spectrometry (JEOL HX110/110 FAB) [M+H] obsd 1280.7, [M+H] calcd 1280.6.

EXAMPLE 28

Preparation of D-Arg-Arg-Pro-4Hyp-Gly-Thi-Ser-(D-4-hydroxyproline trans methyl ether)-Tic-Arg Using the method of Example 26, the peptide D-Arg-Arg-Pro-4Hyp-Gly-Thi-Ser-(D-4-hydroxyproline trans methyl ether)-Tic-Arg was prepared from the appropriate amino acids. Purified peptide was characterized by amino acid analysis and mass spectrometry (JEOL HX110/110 FAB).

EXAMPLE 29

Using the method of Example 26, the peptide D-Arg-Arg-Pro-4Hyp-Gly-Thi-Ser-(D-4-Hydroxyproline trans propyl ether)-Tic-Arg was prepared from the appropriate amino acids. Purified peptide was characterized by amino acid analysis and by mass spectrometry (JEOL HX110/110 FAB).

EXAMPLE 30

Using the method of Example 26, the peptide D-Arg-Arg-Pro-4Hyp-Gly-Thi-Ser-(D-4-Hydroxyproline trans methyl ether)-Oic-Arg was prepared from the appropriate amino acids. Purified peptide was characterized by amino acid analysis and by mass spectrometry (JEOL HX110/110 FAB).

EXAMPLE 31

Preparation of D-Arg-Arg-Pro-4Hyp-Gly-Phe-Ser-(D-4-hydroxyproline trans 4-nitrophenyl ether)-Oic-Arg.

If the method of Example 26 were used, the peptide D-Arg-Arg-Pro-4Hyp-Gly-Phe-Ser-(D-4-hydroxyproline trans 4'-nitrophenyl ether)-Oic-Arg could be prepared. Purified peptide should be characterized by amino acid analysis and have the following results: Arg, 2.95 (3.0); Ser, 0.94 (1.0); Phe, 0.98 (1.0); Gly, 1.0 (1.0).

EXAMPLE 32

Preparation of D-Arg-Arg-Pro-4Hyp-Gly-Phe-Ser-(D-4-hydroxyproline trans napthal thioether)-Oic-Arg.

Using the method of Exaple 26, the peptide D-Arg-Arg-Pro-4Hyp-Gly-Phe-Ser-(D-4-hydroxyproline trans napthal thioether)-Oic-Arg was prepared. Purified peptide was characterized by amino acid analysis and by mass spectrometry (JEOL HX110/110 FAB).

EXAMPLE 33

Preparation of D-Arg-Arg-Pro-4Hyp-Gly-Phe-Ser-(D-4-hydroxyproline cis phenyl thioether)-Oic-Arg.

Using the method of Example 26, the peptide D-Arg-Arg-Pro-4Hyp-Gly-Phe-Ser-(D-4-hydroxyproline cis phenylthioether)-Oic-Arg was characterized by amino acid analysis and by mass spectrometry (JEOL HX110/110 FAB).

EXAMPLE 34

Preparation of D-Arg-Arg-Pro-4Hyp-Gly-Phe-Ser-(D-4-hydroxyproline trans p-chlorophenyl thioether)-Oic-Arg.

Using the method of Example 26, the peptide D-Arg-Arg-Pro-4Hyp-Gly-Phe-Ser-(D-4-hydroxyproline trans p-chlorophenyl thioether)-Oic-Arg was prepared. Purified peptide was characterized by amino acid analysis and by mass spectrometry (JEOL HX110/110 FAB).

EXAMPLE 35

Preparation of D-Arg-Arg-Pro-Pro-Gly-Phe-Ser-(D-4-hydroxyproline trans phenyl thioether)-Oic-Arg.

Using the method of Example 26, the peptide D-Arg-Arg-Pro-Pro-Gly-Phe-Ser-(D-4-hydroxyproline trans phenyl thioether)-Oic-Arg was prepared. Purified peptide was characterized by amino acid analysis and gave the following results: Arg, 3.12 (3.0); Ser, 0.88 (1.0); Phe, 0.99 (1.0); Gly, 1.0 (1.0). The peptide was also characterized by mass spectrometry (JEOL HX110/110 FAB) [M+H] obsd 1328.87, [M+H] calcd 1328.7.

EXAMPLE 36

Preparation of D-Arg-Arg-Pro-4Hyp-Gly-Phe-Ser-(D-4-hydroxyproline cis ethyl ether)-Oic-Arg.

Using the method of Example 26, the peptide D-Arg-Arg-Pro-4Hyp-Gly-Phe-Ser-(D-4-hydroxyproline cis ethyl ether)-Oic-Arg was prepared. Purified peptide was characterized by amino acid analysis and gave the following results: Arg, 3.22 (3.0); Ser, 1.1 (1.0); Phe, 0.99 (1.0); Gly, 1.0 (1.0). The peptide was also characterized by mass spectrometry (JEOL HX110/110 FAB) [M+H] obsd 1280.92, [M+H] calcd 1280.7.

EXAMPLE 37

Preparation of D-Arg-Arg-Pro-4Hyp-Gly-Phe-Ser-(D-4-hydroxyproline trans 2'-nitrophenyl ether)-Oic-Arg.

If the method of Example 26 were used, the peptide D-Arg-Arg-Pro-4Hyp-Gly-Phe-Ser-(D-4-hydroxyproline trans 2'-nitrophenyl ether)-Oic-Arg could be prepared. The purified peptide would be characterized by amino acid analysis and have the following results: Arg, 3.15 (3.0); Ser, 0.81 (1.0); Phe, 1.06 (1.0); Gly, 1.0 (1.0).

EXAMPLE 38

Preparation of D-Arg-Arg-Pro-4Hyp-Gly-Phe-Ser-(D-4-hydroxyproline trans 3'-phenylpropyl ether)-Oic-Arg.

Using the method of Example 26, the peptide D-Arg-Arg-Pro-4Hyp-Gly-Phe-Ser-(D-4-hydroxyproline trans 3'-phenylpropyl ether)-Oic-Arg was prepared. Purified peptide was characterized by amino acid analysis and gave the following results: Arg, 3.13 (3.0); Ser, 0.87 (1.0); Phe, 0.94 (1.0); Gly, 1.0 (1.0). The peptide was also characterized by mass spectrometry (JEOL HX110/110) [M+H] obsd 1370.76, [M+H] cald 1370.8.

EXAMPLE 39

Preparation of D-Arg-Arg-Pro-4Hyp-Gly-Phe-Ser-(D-4-hydroxyproline trans 3'-methylbutyl ether)-Oic-Arg.

Using the method of Example 26, the peptide D-Arg-Arg-Pro-4Hyp-Gly-Phe-Ser-(D-4-hydroxyproline trans 3'-methylbutyl ether)-Oic-Arg was prepared. Purified peptide was characterized by amino acid analysis and gave the following results: Arg, 2.71 (3.0); Ser, 0.77 (1.0); Phe 0.95 (1.0); Gly, 1.0 (1.0). The peptide was also characterized by mass spectrometry (JEOL HX110/110 FAB) [H+H] obsd 1322.82, [M+H] calcd 1322.8.

EXAMPLE 40

Preparation of D-Arg-Arg-Pro-4Hyp-Gly-Thi-Ser-(D-4-hydroxyproline cis methyl ether)-Tic-Arg.

Using the method of Example 26, the peptide D-Arg-Arg-Pro-4Hyp-Gly-Thi-Ser-(D-4-hydroxyproline cis methyl ether)-Tic-Arg was prepared. Purified peptide was characterized by amino acid analysis and gave the following results: Arg, 3.38 (3.0); Ser, 0.84 (1.0); Thi, 1.14 (1.0); Gly, 1.0 (1.0). The peptide was also characterized by mass spectrometry (JEOL HX110/110 FAB) [M+H] obsd 1280.70, [M+H] calcd 1280.6.

EXAMPLE 41

Preparation of D-Arg-Arg-Pro-4Hyp-Gly-Thi-Ser-(D-4-hydroxyproline cis propyl ether)-Tic-Arg.

Using the method of Example 26, the peptide D-Arg-Arg-Pro-4Hyp-Gly-Thi-Ser-(D-4-hydroxyproline cis propyl ether)-Tic-Arg was prepared. Purified peptide was characterized by amino acid analysis and gave the following results: Arg, 3.05 (3.0); Ser, 0.8 (1.0); Thi, 1.08 (1.0); Gly, 1.0 (1.0). The peptide was also characterized by mass spectrometry (JEOL HX110/110 FAB) [M+H] obsd 1308.7, [M+H] calcd 1308.6.

Endotoxin Shock Procedure

Male CF-1 mice (30 g) (Harlan Sprague Dawley) were injected i.v. (0.03 ml) with saline or bradykinin antagonists dissolved in saline. Endotoxin (*Escherichia coli* lipopolysaccharide (LPS) 0.127:B8 Lt 69F4001, Sigma Chemical Co.) was administered in saline (i.p., 50 mg/kg, 0.3 ml). Animals were scored for survival on day 2.

The result of using two inventive formulations are set forth in FIG. 1. The formulations tested were:

A: D-Arg-Arg-Pro-4Hyp-Gly-Phe-Ser-(D-4-hydroxyproline trans thiophenyl ether)-Oic-Arg B: D-Arg-Arg-Pro-4Hyp-Gly-Phe-Ser-(D-4-hydroxyproline trans propylether)-Oic-Arg.

Gram Negative Sepsis Procedure

Male Sprague-Dawley rats (~250 g, Harlan Sprague Dawley, Indianapolis, Ind.) were fasted overnight, anesthetized (isoflurane, 2% v/v) and cannulated via the jugular vein using two indwelling catheters. Fecal peritonitis was initiated by i.p. injection, via a medical incision, of 0.3 ml fecal suspension derived from the coecum of another rat. Gentamicin sulfate (Sigma, St. Louis, Mo.) was given i.v. bolus (2 mg/kg) followed by infusion (2 mg/kg/hr, 0.1 ml/hr) immediately (within 15 minutes) after induction of sepsis and discontinued after 4 days in surviving animals. Bradykinin antagonists were dissolved in 0.1 m sodium phosphate buffer (pH 8) and administered immediately (15 minutes of fecal injection) first i.v. bolus (1 minute) followed by infusion at the indicated doses for the specified duration. In some experiments, bradykinin antagonists were administered therapeutically at various intervals after the induction of fecal peritonitis. Animals surviving the 2 weeks were considered "cured" and experiments were then terminated.

The results are set forth in Tables 1 and 2.

In Table 1, male Sprague Dawley rats were injected (i.p.) with 0.3 ml feces. A single i.v. bolus of gentamicin (2 mg/kg) was given within 15 minutes post sepsis followed by infusion (2 mg/kg/hr) for 4 days in surviving animals. A single (i.v.) bolus dose of Formulation A (1 mg/kg) was given at the indicated time post sepsis followed by infusion (1 mg/kg/hr)

for 4 hours (total dose—5 mg/kg). Values in parenthesis show the number of animals/treatment group.

In Table 2, male rates were injected (i.p.) with 0.3 ml feces. A single bolus (i.v.) of gentamicin (2 mg/kg) or bradykinin antagonists at the indicated dose were given within 15 minutes post sepsis induction, followed by infusion with Formulation A 17761 (0.1 mg/kg/hr to 1 mg/kg/hr) for the indicated times. Gentamicin infusion (2 mg/kg/hr) was discontinued after 4 days in surviving animals. Values in parenthesis represent the number of animals/treatment group.

Bradykinin Binding Procedure

Binding of $^3$H-Bradykinin was preformed using the method of D. C. Manning, R. Vavrek, J. M. Stewart, and S. H. Synder, *J. Pharmacol. Exp. Ther.*, (1986), 237, 504. The tissues used in the binding assay were terminal ileum from male Hartley guinea pigs (150–350 g). After dissection, tissues were placed in 20 vol of ice-cold buffer A (25 mM TES containing 0.2 g/L of 1,10-phenanthroline adjusted to pH 6.8 with ammonium hydroxide) and homogenized using a Ploytron Tissumizer at setting 6 for 15 sec. The homogenate was centrifuged at 50,000 x g for 10 min, the supernatant discarded, and the pellet resuspended in ice-cold buffer A by homogenization with the Polytron. Each tissue was homogenized and centrifuged three times. The final pellet was resuspended in buffer A containing bovine serum albumin (1 g/L) and Bacitracin (0.14 g/L) to a final volume of 170 mL/g of the original tissue weight. The binding assay consisted of 1 mL in 12x75 mm polypropylene tubes: 50 uL $^3$H-bradykinin (20,000 dpm, ~0.3 nM in the final assay volume), 100 L displacing drug in buffer A, and 750 uL tissue homogenate. Each tray contained tubes, to which no drug was added to measure maximum binding and tubes to which bradykinin (1 uM final concentration) had been added, to measure specific binding. Specific binding accounted for 96–98% total binding. Tubes were incubated for 90 min at ambient temperature. The assays were terminated by filtration over Whatman GF/B glass fiber filters that had been pretreated for 2 hours with polyethyleneimine (2 g/L) using a Brandel Tissue Harvester, followed by washing with 4x1 mL aliquots of ice-cold 50 mM Tris, pH 7.4. Filters were dissolved in Ready-Safe Fluor (Beckman) for at least 90 min before quantitation by liquid scintillation spectrometry. Kd values were determined using saturation binding and analysis by EBDA (G. A. MacPherson, *J. Pharmacol. Methods*, (1985), 213), followed by LIGAND (P. J. Munson, D. Rodbard, *Anal. Biochem.*, (1980), 220). Ki values were determined using competitive analysis followed by EBDA and LIGAND. The following test results were obtained.

| Test Compound | Ki (nM) |
|---|---|
| D-Arg-Arg-Pro-4Hyp-Gly-Thi-Ser-(D-4-hydroxyproline cis methyl ether)-Tic-Arg | 164 ± 20 |
| D-Arg-Arg-Pro-4Hyp-Gly-Thi-Ser-(D-4-hydroxyproline cis propyl ether)-Tic-Arg | 172 ± 45 |
| D-Arg-Arg-Pro-4Hyp-Gly-Thi-Ser-(D-4-hydroxyproline trans methyl ether)-Tic-Arg | 1.54 |
| D-Arg-Arg-Pro-4Hyp-Gly-Thi-Ser-(D-4-hydroxyproline trans propyl ether)-Tic-Arg | 0.59 |
| D-Arg-Arg-Pro-4Hyp-Gly-Phe-Ser-(D-4-hydroxyproline trans 4'nitrophenyl ether)-Oic-Arg | 14.47 +\- 2.04 |
| D-Arg-Arg-Pro-4Hyp-Gly-Phe-Ser-(D-4-hydroxyproline trans napthal thioether)-Oic-Arg | 10.14 +\- 4.17 |
| D-Arg-Arg-Pro-4Hyp-Gly-Phe-Ser-(D-4-hydroxyproline cis phenyl thioether)-Oic-Arg | 19.43 +\- 2.67 |
| D-Arg-Arg-Pro-4Hyp-Gly-Phe-Ser-(D-4-hydroxyproline trans-phenyl thioether)-Oic-Arg | 0.05 +\- .02 |
| D-Arg-Arg-Pro-4Hyp-Gly-Phe-Ser-(D-4-hydroxyproline cis ethyl ether)-Oic-Arg | 32.43 +\- 4.83 |
| D-Arg-Arg-Pro-4Hyp-Gly-Phe-Ser-(D-4-hydroxyproline trans 2'-nitrophenyl thioether)-Oic-Arg | 0.36 +\- 0.13 |
| D-Arg-Arg-Pro-4Hyp-Gly-Phe-Ser-(D-4-hydroxyproline trans 3'-phenylpropyl ether)-Oic-Arg | 0.02 +\- 0.01 |
| D-Arg-Arg-Pro-4Hyp-Gly-Phe-Ser-(D-4-hydroxyproline trans 3'-methylbutyl ether)-Oic-Arg | 0.12 +\- 0.01 |
| D-Arg-Arg-Pro-4Hyp-Gly-Phe-Ser-(D-4-hydroxyproline cis methyl ether)-Oic-Arg | 168.67 +\- 20.52 |
| D-Arg-Arg-Pro-4Hyp-Gly-Phe-Ser-(D-4-hydroxyproline cis propyl ether)-Tic-Arg | 172 +\- 45.39 |
| D-Arg-Arg-Pro-4Hyp-Gly-Phe-Ser-(D-4-hydroxyproline trans phenyl ether) | 0.38 +\- 0.11 |
| D-Arg-Arg-Pro-4Hyp-Gly-Phe-Ser-(D-4-hydroxyproline trans ethyl ether)-Oic-Arg | 0.42 +\- 0.06 |
| D-Arg-Arg-Pro-4Hyp-Gly-Phe-Ser-(D-4-hydroxyproline trans propyl ether)-Oic-Arg | 0.16 +\- 0.04 |
| D-Arg-Arg-Pro-Pro-Gly-Phe-Ser-(D-4-hydroxyproline trans propyl ether)-Oic-Arg | 0.5 +\- 0.16 |

Determination of Bradykinin Antagonist Activity

This protocol was designed to identify compounds that possess antagonist activity at bradykinin receptors on intestinal (ileal longitudinal) smooth muscle.

Guinea pig intestine was removed and placed in a Petri dish containing Tyrodes solution and cut into 3–4 cm segments. The longitudinal muscle was separated from the underlying circular muscle using a cotton applicator (Paton and Zar, *J. Physiol.*, (1968), 194:13. Muscle strips were connected to isometric force-displacement transducers (Grass or Gould) coupled to a physiograph and placed in tissue baths containing Tyrode's solution at 37° C. Each preparation was suspended under a resting tension of 2 g.

After equilibration of the tissues, appropriate volumes of bradykinin solutions were cumulatively added to the 10 mL tissue baths to increase the concentration of bradykinin in the bath step-by-step without washing out after each single dose. Higher concentrations were added only after the preceding contraction had reached a steady value. When the next concentration step does not cause a further increase in contraction, it was assumed that the maximum effect had been obtained and the tissue was washed to remove bradykinin and allowed to recover for 15 minutes. Antagonism of bradykinin responses in the presence of antagonist were determined by repeating the cumulative addition procedure for bradykinin after the tissue has been exposed to the antagonist for 5 minutes. Three or four different concentrations of antagonist are studied sequentially in the same preparations. Responses were expressed as a percentage of the maximum contraction elicited by bradykinin in the absence of antagonist. $pA_2$ values were calculated by Schild analysis. The following results were obtained.

| Test Compound | $pA_2$ |
|---|---|
| D-Arg-Arg-Pro-4Hyp-Gly-Thi-Ser-(D-4-hydroxyproline cis methyl ether)-Tic-Arg | 5.2 |
| D-Arg-Arg-Pro-4Hyp-Gly-Thi-Ser-(D-4-hydroxyproline cis propyl ether)-Tic-Arg | 5.50 |
| D-Arg-Arg-Pro-4Hyp-Gly-Thi-Ser-(D-4-hydroxyproline trans methyl ether)-Tic-Arg | 6.73 |
| D-Arg-Arg-Pro-Pro-Gly-Phe-Ser-(D-4-hydroxyproline trans phenyl thioether)-Oic-Arg | 7.96 +\- 0.05 |

-continued

| Test Compound | pA₂ |
|---|---|
| D-Arg-Arg-Pro-4Hyp-Gly-Phe-Ser-(D-4-hydroxyproline cis ethyl ether)-Oic-Arg | 5.49 +\- 0.09 |
| D-Arg-Arg-Pro-4Hyp-Gly-Thi-Ser-(D-4-hydroxyproline cis methyl ether)-Tic-Arg | 5.24 +\- 0.01 |
| D-Arg-Arg-Pro-4Hyp-Gly-Thi-Ser-(D-4-hydroxyproline trans propyl ether)-Oic-Arg | 8.54 +\- 0.02 |
| D-Arg-Arg-Pro-4Hyp-Gly-Thi-Ser-(D-4-hydroxyproline trans 2'-nitrophenyl ether)-Oic-Arg | 8.10 +\- 0.06 |
| D-Arg-Arg-Pro-4Hyp-Gly-Phe-Ser-(D-4-hydroxyproline trans phenyl thioether)-Oic-Arg | 8.05 +\- 0.17 |
| D-Arg-Arg-Pro-4Hyp-Gly-Phe-Ser-(D-4-hydroxyproline trans propyl ether)-Oic-Arg | 7.67 +\- 0.02 |
| D-Arg-Arg-Pro-Pro-Gly-Phe-Ser-(D-4-hydroxyproline trans propyl ether)-Oic-Arg | 7.89 +\- 0.02 |
| D-Arg-Arg-Pro-Pro-Gly-Phe-Ser-(D-4-hydroxyproline trans phenyl ether)-Oic-Arg | 5.24 +\- 0.01 |
| D-Arg-Arg-Pro-4Hyp-Gly-Thi-Ser-(D-4-hydroxyproline trans propyl ether)-Tic-Arg | 7.61 +\- 0.03 |
| D-Arg-Arg-Pro-4Hyp-Gly-Thi-Ser-(D-4-hydroxyproline cis propyl ether)-Tic-Arg | 5.05 +\- 0.03 |
| D-Arg-Arg-Pro-4Hyp-Gly-Phe-Ser-D-Phe-Phe-Arg (Standard Reference) | 5.9 |

The invention being thus described, it will be obvious that the same may be varied in many ways. Such variations are not to be regarded as a departure from the spirit and scope of the invention and all such modifications are intended to be included within the scope of the following claims.

G is a direct bond or is selected from the group consisting of Ser, Thr, 4Hyp, Gly, Val, and Ala;

H is a compound of the D-configuration having the formula:

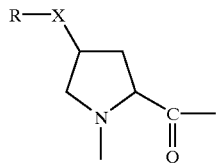

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1$NHC(o)— where $R^1$ is $C_1$–$C_6$ alkyl or aryl, and where X is either, sulfur or oxygen;

I is selected from the group consisting of Oic, Aoc, Thz, Tic, L-indoline-2-carboxylic acid, octahydro-1H-isoindole-1-carboxylic acid, pipecolinic acid, Pro, 4Hyp, azetidine-2-carboxylic acid, Aib, Leu, Ile, Val, Thi, Phe, and homoPhe, and compounds of the following formula:

What is claimed is:

1. A peptide having the formula:

N-A-B-C-D-E-F-G-H-I-J-Cn wherein N is hydrogen;

A and B are independently selected from the group consisting of L-Arg, D-Arg, L-Gln, D-Gln, D-Asn, L-Asn, N-ε-acetyl-D-lysine, ε-acetyl-L-lysine, $N^G$-p-tosyl-Arg, $N^G$-nitro-Arg, Lys—Lys, acetyl-D-Arg, L-Citrulline, L-Lys, Sar, and D-Lys;

C and D are a direct bond or are independently selected from the group consisting of Pro, dehydroPro, 4Hyp, Tic, Aoc, Ala, L-azetidine-2-carboxylic acid, Eac, Gly, Thz, Oic, and Aib;

E is a direct bond or is selected from the group consisting of Gly, Ala, Thr, and Ser;

F is selected from the group consisting of Phe, Thi, Leu, Ile, Tic, Oic, homoPhe, phenylGly, β-cyclohexylalanine, Nal, and Val;

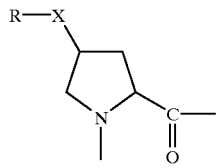

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1$NHC(o)— where $R^1$ is $C_1$–$C_6$ alkyl or aryl, and where X is either sulfur or oxygen;

J is selected from the group consisting of Arg, Orn, Asn, Gln, N-ε-acetyl-Lys, N-δ-acetyl-Orn, and Lys;

Cn is a hydroxyl group or a C-terminal extension selected from the group consisting of amide, alkoxy group, an acidic, basic, or neutral aliphatic aromatic, cyclic amino acid residue of the D- or L-configuration, and a peptide extension composed of D- or L-amino acids;

and pharmaceutically acceptable salts thereof.

2. A peptide of claim 1 wherein:

A and B are independently selected from the group consisting of L-Arg, D-Arg, Lys—Lys, Lys;

C and D are independently selected from the group consisting of Pro, dehydroPro, and 4Hyp;

E is Gly;

F is selected from the group consisting of Phe, Thi, Leu, and β-cyclohexylalanine;

G is direct bond or is selected from the group consisting of Ser and Thr;

H is a compound of the D-configuration having the formula:

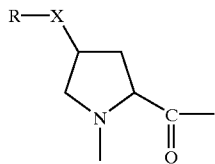

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either sulfur or oxygen;

I is selected from the group consisting of Oic, Aoc, Thz, Pro, pipecolinic acid, Leu, Phe, Thi, Tic and compounds of the following formula:

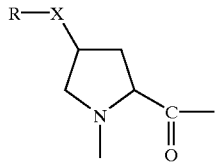

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either sulfur or oxygen;

J is selected from the group consisting of Arg and Lys;

Cn is a hydroxyl group;

and pharmaceutically acceptable salts thereof.

3. A peptide of claim 1 wherein:

A is D-Arg;

B is Arg;

C and D are independently selected from the group consisting of Pro and 4Hyp;

E is Gly;

F is Phe;

G is Ser;

H is a compound of the D-configuration having the formula:

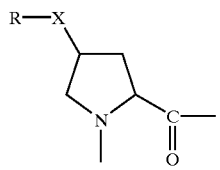

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either sulfur or oxygen;

I is selected from the group consisting of Tic, Aoc, and Oic;

J is Arg;

Cn is a hydroxyl group;

and pharmaceutically acceptable salts thereof.

4. A peptide of claim 1 wherein:

A is D-Arg;

B is Arg;

C and D are independently selected from the group consisting of Pro and 4Hyp;

E is Gly;

F is selected from the group consisting of Phe and Thi;

G is Ser;

H is a compound of the D-configuration having the formula:

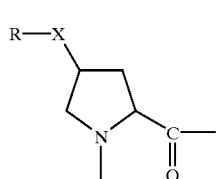

wherein R is selected from the group consisting of $C_1$–$C_6$ alkyl, substituted $C_1$–$C_6$ alkyl, $C_2$–$C_8$ alkenyl, $C_3$–$C_8$ cycloalkyl, $C_3$–$C_8$ cycloalkyl substituted $C_1$–$C_6$ alkyl, an aryl group, a substituted aryl group, an arylalkyl group, and a group of the formula $R^1NHC(o)$— where $R^1$ is $C_1$–$C_6$ alkyl or aryl, and where X is either sulfur or oxygen;

I is Oic;

J is Arg;

Cn is a hydroxyl group;

and pharmaceutically acceptable salts thereof.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Mammalian

<400> SEQUENCE: 1

Arg Pro Pro Gly Phe Ser Pro Phe Arg